(12) United States Patent
Lang et al.

(10) Patent No.: US 10,485,676 B2
(45) Date of Patent: Nov. 26, 2019

(54) SOLID FREEFORM FABRICATION OF IMPLANT COMPONENTS

(71) Applicant: ConforMIS, Inc., Billerica, MA (US)

(72) Inventors: Philipp Lang, Lexington, MA (US); John Slamin, Wrentham, MA (US)

(73) Assignee: ConforMIS, Inc., Billerica, MA (US)

( * ) Notice: Subject to any disclaimer, the term of this patent is extended or adjusted under 35 U.S.C. 154(b) by 92 days.

(21) Appl. No.: 15/582,994

(22) Filed: May 1, 2017

(65) Prior Publication Data

US 2017/0231783 A1 Aug. 17, 2017

Related U.S. Application Data

(62) Division of application No. 14/033,095, filed on Sep. 20, 2013, now Pat. No. 9,636,229.

(Continued)

(51) Int. Cl.
*A61F 2/46* (2006.01)
*A61F 2/38* (2006.01)
*B33Y 80/00* (2015.01)
*B33Y 10/00* (2015.01)
*B33Y 50/02* (2015.01)
*B23K 26/342* (2014.01)

(Continued)

(52) U.S. Cl.
CPC ............. *A61F 2/461* (2013.01); *A61F 2/389* (2013.01); *B22F 3/1055* (2013.01); *B23K 15/0086* (2013.01); *B23K 26/342* (2015.10); *B33Y 10/00* (2014.12); *B33Y 50/02* (2014.12); *B33Y 80/00* (2014.12); *A61B 17/1764* (2013.01); *A61B 2034/102* (2016.02); *A61F 2002/30561* (2013.01); *A61F 2002/30878* (2013.01); *A61F 2002/30962* (2013.01); *A61F 2002/30985* (2013.01); *A61F 2002/4495* (2013.01); *A61F 2002/4619* (2013.01); *B22F 2998/10* (2013.01); *B33Y 50/00* (2014.12); *Y10T 29/49* (2015.01)

(58) Field of Classification Search
CPC .. A61F 2/389; A61F 2/461; A61F 2002/4619; A61B 17/1764
See application file for complete search history.

(56) References Cited

U.S. PATENT DOCUMENTS 4,673,409 A 6/1987 Van Kampen
5,067,964 A 11/1991 Richmond et al.
(Continued)

FOREIGN PATENT DOCUMENTS

DE 3933459 A1 4/1991
DE 4434539 C2 6/1998
(Continued)

OTHER PUBLICATIONS

"Biemond et al. "Bone ingrowth potential of electron beam and selective laser melting produced trabecular-like implant surfaces with and without a biomimetic coating," Journal of Materials Science Materials in Medicine, vol. 24, No. 3, pp. 745-753, Dec. 21, 2012 (abstract only)".

(Continued)

*Primary Examiner* — Jason-Dennis N Stewart
(74) *Attorney, Agent, or Firm* — Sunstein Kann Murphy & Timbers LLP

(57) ABSTRACT

Disclosed are designs, methods and systems for manufacturing implants, implant components, features of implant components, and/or related tools using solid freeform fabrication or additive metals technologies.

10 Claims, 13 Drawing Sheets

Related U.S. Application Data

(60) Provisional application No. 61/703,768, filed on Sep. 20, 2012, provisional application No. 61/801,992, filed on Mar. 15, 2013.

(51) Int. Cl.

| | | |
|---|---|---|
| *B22F 3/105* | (2006.01) | |
| *B23K 15/00* | (2006.01) | |
| *B33Y 50/00* | (2015.01) | |
| *A61F 2/30* | (2006.01) | |
| *A61F 2/44* | (2006.01) | |
| *A61B 17/17* | (2006.01) | |
| *A61B 34/10* | (2016.01) | |

(56) References Cited

U.S. PATENT DOCUMENTS

| | | |
|---|---|---|
| 5,246,530 A | 9/1993 | Bugle et al. |
| 5,365,996 A | 11/1994 | Crook |
| 5,507,820 A | 4/1996 | Pappas |
| 5,735,277 A | 4/1998 | Schuster |
| 6,112,109 A | 8/2000 | D'urso |
| 6,206,927 B1 | 3/2001 | Fell et al. |
| 6,251,143 B1 | 6/2001 | Schwartz et al. |
| 6,254,639 B1 | 7/2001 | Peckitt |
| 6,280,478 B1 | 8/2001 | Richter et al. |
| 6,510,334 B1 | 1/2003 | Schuster et al. |
| 6,527,810 B2 | 3/2003 | Johnson et al. |
| 6,540,786 B2 | 4/2003 | Chibrac et al. |
| 6,632,246 B1 | 10/2003 | Simon et al. |
| 6,677,554 B2 | 1/2004 | Darrah et al. |
| 6,679,917 B2 | 1/2004 | Ek |
| 6,694,207 B2 | 2/2004 | Darrah et al. |
| 6,712,856 B1 | 3/2004 | Carignan et al. |
| 6,799,066 B2 | 9/2004 | Steines et al. |
| 6,905,514 B2 | 6/2005 | Carignan et al. |
| 6,932,842 B1 | 8/2005 | Litschko et al. |
| 6,978,188 B1 | 12/2005 | Christensen |
| 7,001,672 B2 | 2/2006 | Justin et al. |
| 7,172,596 B2 | 2/2007 | Coon et al. |
| 7,239,908 B1 | 7/2007 | Alexander et al. |
| 7,368,065 B2 | 5/2008 | Yang et al. |
| 7,445,640 B2 | 11/2008 | Despres, III |
| 7,468,075 B2 | 12/2008 | Lang et al. |
| 7,603,192 B2 | 10/2009 | Martin et al. |
| 7,632,575 B2 | 12/2009 | Justin et al. |
| 7,718,109 B2 | 5/2010 | Robb et al. |
| 7,983,777 B2 | 7/2011 | Melton et al. |
| 8,021,154 B2 | 9/2011 | Holzner et al. |
| 8,070,752 B2 | 12/2011 | Metzger et al. |
| 8,086,336 B2 | 12/2011 | Christensen |
| 8,092,462 B2 | 1/2012 | Pinczewski et al. |
| 8,142,886 B2 | 3/2012 | Noble et al. |
| 8,160,345 B2 | 4/2012 | Pavlovskaia et al. |
| 8,221,430 B2 | 7/2012 | Park et al. |
| 8,282,646 B2 | 10/2012 | Schoenefeld et al. |
| 8,311,306 B2 | 11/2012 | Pavlovskaia et al. |
| 8,329,202 B2 | 12/2012 | Perla et al. |
| 8,337,508 B2 | 12/2012 | Lavallee et al. |
| 8,357,166 B2 | 1/2013 | Aram et al. |
| 8,377,066 B2 | 2/2013 | Katrana et al. |
| 8,377,068 B2 | 2/2013 | Aker et al. |
| 8,380,471 B2 | 2/2013 | Iannotti et al. |
| 8,398,646 B2 | 3/2013 | Metzger et al. |
| 8,407,067 B2 | 3/2013 | Uthgenannt et al. |
| 8,419,740 B2 | 4/2013 | Aram et al. |
| 8,425,524 B2 | 4/2013 | Aker et al. |
| 8,457,930 B2 | 6/2013 | Schroeder |
| 8,617,242 B2 | 12/2013 | Philipp |
| 8,735,773 B2 | 5/2014 | Lang |
| 8,801,720 B2 | 8/2014 | Park et al. |
| 9,408,686 B1 | 8/2016 | Miller et al. |
| 9,439,767 B2 | 9/2016 | Bojarski et al. |
| 9,517,134 B2 | 12/2016 | Lang et al. |
| 9,579,110 B2 | 2/2017 | Bojarski et al. |
| 9,636,229 B2 | 5/2017 | Lang et al. |
| 9,700,971 B2 | 7/2017 | Lang et al. |
| 9,849,019 B2 | 12/2017 | Miller et al. |
| 2002/0028980 A1 | 3/2002 | Thierfelder et al. |
| 2002/0059049 A1 | 5/2002 | Bradbury et al. |
| 2002/0079601 A1 | 6/2002 | Russell et al. |
| 2002/0082741 A1 | 6/2002 | Mazumder et al. |
| 2003/0080957 A1 | 5/2003 | Stewart et al. |
| 2003/0236473 A1 | 12/2003 | Dore et al. |
| 2004/0098133 A1 | 5/2004 | Carignan et al. |
| 2004/0102866 A1 | 5/2004 | Harris et al. |
| 2004/0117015 A1 | 6/2004 | Biscup |
| 2005/0119664 A1 | 6/2005 | Carignan et al. |
| 2005/0137601 A1 | 6/2005 | Assell et al. |
| 2005/0148843 A1 | 7/2005 | Roose et al. |
| 2005/0244239 A1 | 11/2005 | Shimp |
| 2005/0267584 A1 | 12/2005 | Burdulis, Jr. et al. |
| 2006/0069318 A1 | 3/2006 | Keaveny et al. |
| 2006/0136058 A1 | 6/2006 | Pietrzak |
| 2006/0241776 A1 | 10/2006 | Brown et al. |
| 2007/0005143 A1 | 1/2007 | Ek et al. |
| 2007/0118055 A1 | 5/2007 | McCombs |
| 2007/0118243 A1 | 5/2007 | Schroeder et al. |
| 2007/0142914 A1 | 6/2007 | Jones et al. |
| 2007/0198022 A1 | 8/2007 | Lang et al. |
| 2007/0226986 A1 | 10/2007 | Park et al. |
| 2007/0233141 A1 | 10/2007 | Park et al. |
| 2007/0288030 A1 | 12/2007 | Metzger et al. |
| 2008/0004709 A1 | 1/2008 | O'Neill et al. |
| 2008/0114370 A1 | 5/2008 | Schoenefeld et al. |
| 2008/0147072 A1 | 6/2008 | Park et al. |
| 2008/0195216 A1 | 8/2008 | Philipp |
| 2008/0215059 A1 | 9/2008 | Carignan et al. |
| 2008/0257363 A1 | 10/2008 | Schoenefeld et al. |
| 2008/0262624 A1 | 10/2008 | White et al. |
| 2009/0072447 A1 | 3/2009 | Hull et al. |
| 2009/0088753 A1 | 4/2009 | Aram et al. |
| 2009/0099567 A1 | 4/2009 | Zajac |
| 2009/0110498 A1 | 4/2009 | Park |
| 2009/0131941 A1 | 5/2009 | Park et al. |
| 2009/0138020 A1 | 5/2009 | Park et al. |
| 2009/0151736 A1 | 6/2009 | Belcher et al. |
| 2009/0226068 A1 | 9/2009 | Fitz et al. |
| 2010/0049195 A1 | 2/2010 | Park et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0217270 A1 | 8/2010 | Polinski et al. |
| 2010/0256479 A1 | 10/2010 | Park et al. |
| 2010/0332194 A1 | 12/2010 | McGuan et al. |
| 2011/0029091 A1 | 2/2011 | Bojarski et al. |
| 2011/0029093 A1 | 2/2011 | Bojarski et al. |
| 2011/0071533 A1 | 3/2011 | Metzger et al. |
| 2011/0087332 A1 | 4/2011 | Bojarski et al. |
| 2011/0092804 A1 | 4/2011 | Schoenefeld et al. |
| 2011/0218545 A1 | 9/2011 | Catanzarite et al. |
| 2011/0264097 A1 | 10/2011 | Hodorek et al. |
| 2011/0266265 A1 | 11/2011 | Lang |
| 2012/0022659 A1 | 1/2012 | Wentorf et al. |
| 2012/0078598 A1 | 3/2012 | McDaniel |
| 2012/0116203 A1 | 5/2012 | Vancraen et al. |
| 2012/0141034 A1 | 6/2012 | Iannotti et al. |
| 2012/0239045 A1 | 9/2012 | Li |
| 2012/0265496 A1 | 10/2012 | Mahfouz |
| 2012/0276509 A1 | 11/2012 | Iannotti et al. |
| 2012/0310364 A1 | 12/2012 | Li et al. |
| 2012/0316564 A1 | 12/2012 | Serbousek et al. |
| 2012/0323246 A1 | 12/2012 | Catanzarite et al. |
| 2013/0006250 A1 | 1/2013 | Metzger et al. |
| 2013/0035766 A1 | 2/2013 | Meridew |
| 2013/0066321 A1 | 3/2013 | Mannss et al. |
| 2013/0119579 A1 | 5/2013 | Iannotti et al. |
| 2013/0171019 A1 | 7/2013 | Gessler et al. |
| 2013/0204384 A1 | 8/2013 | Hensley et al. |
| 2013/0220570 A1 | 8/2013 | Sears et al. |
| 2013/0245803 A1 | 9/2013 | Lang |
| 2013/0253522 A1 | 9/2013 | Bojarski et al. |
| 2014/0039631 A1 | 2/2014 | Bojarski et al. |
| 2014/0065194 A1 | 3/2014 | Yoo et al. |

(56) References Cited

U.S. PATENT DOCUMENTS

| | | |
|---|---|---|
| 2014/0086780 A1 | 3/2014 | Miller et al. |
| 2014/0109384 A1 | 4/2014 | Lang |
| 2014/0172111 A1 | 6/2014 | Lang et al. |
| 2014/0250677 A1 | 9/2014 | Lang |
| 2014/0259629 A1 | 9/2014 | Dion et al. |
| 2014/0324205 A1 | 10/2014 | Park et al. |
| 2015/0081029 A1 | 3/2015 | Bojarski et al. |
| 2015/0093283 A1 | 4/2015 | Miller et al. |
| 2017/0112626 A1 | 4/2017 | Miller et al. |
| 2017/0119531 A1 | 5/2017 | Bojarski et al. |
| 2017/0164957 A1 | 6/2017 | Bojarski et al. |
| 2017/0231783 A1 | 8/2017 | Lang et al. |

FOREIGN PATENT DOCUMENTS

| | | |
|---|---|---|
| DE | 10055465 A1 | 5/2002 |
| DE | 102006037067 B4 | 6/2011 |
| EP | 0704193 A1 | 4/1996 |
| EP | 1074229 B1 | 10/2005 |
| EP | 1683593 A2 | 7/2006 |
| EP | 1800700 A2 | 6/2007 |
| EP | 2173260 B1 | 1/2012 |
| JP | H07236648 A | 9/1995 |
| JP | H0825487 A | 1/1996 |
| JP | H09169056 A | 6/1997 |
| JP | 2004166802 A | 6/2004 |
| JP | 2005532089 A | 10/2005 |
| JP | 2007236926 A | 9/2007 |
| JP | 2010538882 A | 12/2010 |
| WO | WO-9325157 A1 | 12/1993 |
| WO | WO-0177988 A2 | 10/2001 |
| WO | WO-03094782 A2 | 11/2003 |
| WO | WO-2004047688 A1 | 6/2004 |
| WO | WO-2005002473 A1 | 1/2005 |
| WO | WO-2008021494 A2 | 2/2008 |
| WO | WO-2008101090 A2 | 8/2008 |
| WO | WO-2009001083 A1 | 12/2008 |
| WO | WO-2009039159 A2 | 3/2009 |
| WO | WO-2009068892 A1 | 6/2009 |
| WO | WO-2009106366 A1 | 9/2009 |
| WO | WO-2009106816 A1 | 9/2009 |
| WO | WO-2010099359 A1 | 9/2010 |
| WO | WO-2010148103 A1 | 12/2010 |
| WO | WO-2011028624 A1 | 3/2011 |
| WO | WO-2011056995 A2 | 5/2011 |
| WO | WO-2011059641 A1 | 5/2011 |
| WO | WO-2011094540 A2 | 8/2011 |
| WO | WO-2011101474 A1 | 8/2011 |
| WO | WO-2011109260 A1 | 9/2011 |
| WO | WO-2011130421 A1 | 10/2011 |
| WO | WO-2012021241 A2 | 2/2012 |
| WO | WO-2012021846 A2 | 2/2012 |
| WO | WO-2012021894 A2 | 2/2012 |
| WO | WO-2012021895 A2 | 2/2012 |
| WO | WO-2012027150 A2 | 3/2012 |
| WO | WO-2012051542 A2 | 4/2012 |
| WO | WO-2012112698 A2 | 8/2012 |
| WO | WO-2013152341 A1 | 10/2013 |
| WO | WO-2013155500 A1 | 10/2013 |
| WO | WO-2014047514 A1 | 3/2014 |

OTHER PUBLICATIONS

Birnbaum et al. "Computer-Assisted Orthopedic Surgery With Individual Templates and Comparison to Conventional Operation Method", Spine, vol. 26, No. 4, pp. 365-369, Feb. 2001.
Brandt et al. "CRIGOS—Development of a Compact Robot System for Image-Guided Orthopedic Surgery," Der Orthopäde, Springer-Verlag, vol. 29, No. 7, pp. 645-649 (Jul. 2000) (English Translation with Certification).
Brandt et al. "CRIGOS—Development of a Compact Robot System for Image-Guided Orthopedic Surgery," Der Orthopäde, Springer-Verlag, vol. 29, No. 7, pp. 645-649 (Jul. 2000) (In German).
Chelule et al. "Computer Aided Design of Personalized Jigs in Total Knee Replacement", 3rd Annual Meeting of CAOS Int'l Proc., Spain, Jun. 18, 21, 2003, pp. 58-59.
Chelule et al. "Patient-Specific Template to Preserve Bone Stock in Total Knee Replacement: Preliminary Results", 15th Annual ISTA Symposium, Sep. 2002, 1 page.
Extended European Search Report—Application No. 12192903.8-1654 dated Apr. 17, 2013, 8 pages.
Extended European Search Report—Application No. 13775348.9-1654 dated Mar. 10, 2015, 6 pages.
Froemel et al. "Computer Assisted Template Based Navigation for Total Knee Replacement", Documents presented at CAOS on Jun. 17, 2001, 4 pages.
Hafez et al. "Computer Assisted Total Knee Replacement: Could a Two-Piece Custom Template Replace the Complex Conventional Instrumentations?", 4th Annual Meeting of CAOS Int'l Proc., Chicago, Jun. 16-19, 2004, pp. 63-64.
Hafez et al. "Computer Assisted Total Knee Replacement: Could a Two-Piece Custom Template Replace the Complex Conventional Instrumentations?" Session 6: Novel Instruments; Computer Aided Surgery, Session 6, vol. 9, No. 3, pp. 93-94 (Jun. 2004).
Hafez et al. "Computer-Assisted Total Hip Arthroplasty: The Present and the Future", Future Rheumatol., vol. 1, pp. 121-131, 2006.
Hafez et al. "Computer-assisted Total Knee Arthroplasty Using Patient-specific Templating," Clinical Orthopaedics and Related Research, No. 444, pp. 184-192 (Mar. 2006).
International Search Report—International Application No. PCT/US2008/053977, dated Sep. 30, 2008, together with the Written Opinion of the International Searching Authority, 17 pages.
International Search Report—International Application No. PCT/US2012/025274 dated Oct. 25, 2012, together with the Written Opinion of the International Searching Authority, 12 pages.
International Search Report—International Application No. PCT/US2013/035536 dated Jul. 18, 2013, together with the Written Opinion of the International Searching Authority, 9 pages.
International Search Report—International Application No. PCT/US2013/036505 dated Jul. 29, 2013, together with the Written Opinion of the International Searching Authority, 7 pages.
International Search Report—International Application No. PCT/US2013/061042 dated Jan. 10, 2014, together with the Written Opinion of the International Searching Authority, 12 pages.
Invitation to Pay Additional Fees—International Application No. PCT/US2008/053977, dated Jul. 11, 2008, together with the Written Opinion of the International Searching Authority, 6 pages.
Mumtaz et al. "Selective Laser Melting of Inconel 625 Using Pulse Shaping", Rapid Prototyping Journal, ® vol. 16, Iss. 4, pp. 248-257, 2010.
"Office Action pertaining to Japanese Patent Application No. 2015-505970 dated Nov. 24, 2015, 2 pages ( In Japanese)".
"Office Action pertaining to Japanese Patent Application No. 2015-505970 dated Nov. 24, 2015, 4 pages (English translation)".
Partial Supplementary European Search Report—Application No. 13771863.1-1654, dated Apr. 26, 2016, 7 pages.
Petrovic et al. "Additive Manufacturing Solutions for Improved Medical Implants", Biomedicine, INTECH, pp. 148-180, Mar. 2012.
Portheine et al. "Computer-Assisted Total Knee Endoprosthetics with Planning-Specific Treatment Templates", Biomed. Tech., vol. 46, Supp. vol. 1, Jan. 2001—English translation.
Portheine et al. "Computer-Assisted Total Knee Endoprosthetics with Planning-Specific Treatment Templates", Biomed. Tech., vol. 46, Supp. vol. 1, Jan. 2001—In German.
Portheine et al CT-Based Planning and Individual Template Navigation in TKA Navigation and Robotics in Total Joint and Spine Surgery Springer 48:336-342 (2004).
Portheine et al. Development of a clinical demonstrator for computer assisted orthopedic surgery with CT-image based individual templates Computer Assisted Radiology and Surgery (1997).
Portheine et al. "Potentials of CT-based Planning and Template-based Procedure in Hip and Knee Surgery", Orth. Prac., vol. 36, pp. 786-791, 2000—English Translation.

(56) References Cited

OTHER PUBLICATIONS

Portheine et al. "Potentials of CT-based Planning and Template-based Procedure in Hip and Knee Surgery", Orth. Prac., vol. 36, pp. 786-791, 2000—In German.
Portheine thesis : "Model-Based Operation Planning in Orthopedic Surgery", Thesis, RWTH Aachen University, Apr. 22, 2004, 90 pages—In German.
Portheine thesis "Model-Based Operation Planning in Orthopedic Surgery", Thesis, RWTH Aachen University, Apr. 22, 2004, 170 pages—English Translation.
Pulido et al."A Randomized Clinical Trial of 260 TKA: Porous-Metal Tibial Components were Reliable".
Radermacher "Computer Assisted Matching of Planning and Execution in Orthopedic Surgery", Slide Presentation, San Diego, Nov. 29, 1993, 22 pages.
Radermacher "Computer-Based Decision Support in the Selection and Evaluation of Contact Surfaces for Manual Referencing", Lecture presented at Helmholtz Meeting '98 and OSS '98, 6 pages (1998)—®In German.
Radermacher "Computer-Based Decision Support in the Selection and Evaluation of Contact Surfaces for Manual Referencing", Lecture presented at Helmholtz Meeting '98 and OSS '98, 8 pages (1998)—English Translation.
Radermacher et al. Image Guided Orthopedic Surgery Using Individual Templates Experimental Results and Aspects of the Development of a Demonstrator for Pelvis Surgery in Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-616, 1997.
Radermacher et al. "Computer Assisted Matching of Planning and Execution in Orthopedic Surgery", IEEE, EMBS, San Diego, 1993, pp. 946-947.
Radermacher et al. "Computer Assisted Orthopedic Surgery by Means of Individual Templates •Aspects and Analysis of Potential Applications •" Proceedings of the First International Symposium on Medical Robotics and Computer Assisted Surgery, vol. 1: Sessions I-III MRCAS '94, Pittsburgh, PA, pp. 42-48 (Sep. 22-24, 1994).
Radermacher et al. "Computer Based Decision Support for the Planning of Contact Faces for Manual Registration with Individual Templates", Helmholtz-Institute for Biomed. Eng., 7 pages, 1997-98.
Radermacher et al. "Computer Integrated Advanced Orthopedics (CIAO)", 2nd European Conference on Eng. and Med., presented Apr. 26, 1993, 12 pages.
Radermacher et al. "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher et al. "Computer-assisted operative interventions in orthopedics—are there prospects for endoprosthetics as well?", Prac. Ortho., vol. 27, pp. 1-17, 1997—English Translation.
Radermacher et al. "Computer-assisted operative interventions in orthopedics—are there prospects for endoprosthetics as well?", Prac. Ortho., vol. 27, pp. 149-164, 1997—In German.
Radermacher et al. "Computer-Assisted Planning and Operation in Orthopedics", Orth. Prac. 36th year, pp. 731-737, Dec. 2000—English Translation.
Radermacher et al. "Computer-Assisted Planning and Operation in Orthopedics", Orth. Prac. 36th year, pp. 731-737, Dec. 2000—In German.
Radermacher, et al. CT Image Based Planning and Execution of Interventions in Orthopedic Surgery Using Individual Templates Experimental Results and Aspects of Clinical Applications. In Nolte LP, Ganz, R. (eds). CAOS Computer Assisted Orthopaedic Surgery. Bern, Hans Huber (In Press) 1998.
Radermacher et al. Technique for Better Execution of CT Scan Planned Orthopedic Surgery on Bone Structures. In Lemke HW Inamura K. Jaffe CC Vannier MW (eds). Computer Assisted Radiology Berlin Springer 933-938 1995.
Radermacher et al. "Surgical Therapy Technology", Helmholtz-Institut Aachen Research Report, 1993-1994, pp. 189-219.
Radermacher "Image Guided Orthopedic Surgery with Individual Templates", Helmhotz-Institute for Biomed. Eng., 2 pages, 1997.
Radermacher K. et al. Computer Integrated Orthopedic Surgery Connection of Planning and Execution in Surgical Inventions. In Taylor R. Lavallee S. Burdea G. Mosges R. (eds). Computer Integrated Surgery. Cambridge MIT press 451-463 1996.
Radermacher Klaus Computer Assisted Orthopaedic Surgery With Image Based Individual Templates Clinical Orthopaedics Sep. 1998 vol. 354 pp. 28-38.
Radermacher Klaus English Translation: Helmholtz Institute of Biomedical Technology Computer-Assisted Planning and Execution of Orthopedic Surgery Using Individual Surgical Templates May 18, 1999.
Radermacher Klaus German Version: Helmholtz Institute of Biomedical Technology Computer-Assisted Planning and Execution of Orthopedic Surgery Using Individual Surgical Templates May 18, 1999.
Radermacher "Template Based Navigation—An Efficient Technique for Hip and Knee Surgery", CAOS First Asian Meet, India, Mar. 27-28, 2004, pp. 44-50.
Rau et al. "Small and Neat", Medical Tech. Int'l, pp. 65, 67 and 69, 1993-94.
Schiffers et al. "Planning and execution of orthopedic surgery using individualized templates," Der Orthopäde, Springer-Verlag, vol. 29, No. 7, pp. 636-640, (Jul. 2000) (In German).
Schiffers et al. "Planning and execution of orthopedic surgery using individualized templates," Der Orthopäde, Springer-Verlag, vol. 29, No. 7, pp. 636-640, (Jul. 2000) (English Translation with Certification).
Schkommodau et al. "Clinical Application of Individual Templates for Pedicle Screw Placement in Comparison to Computer Navigation", Poster presented at CAOS, Feb. 18, 2000, 1 page.
Schkommodau et al. "Clinical Experience With the Individual Template Technique", Orth. Prac., vol. 37, No. 1, pp. 19-22, 2001—English Translation.
Schkommodau et al. "Clinical Experience With the Individual Template Technique", Orth. Prac., vol. 37, No. 1, pp. 19-22, 2001—In German.
Seel et al. "Three-Dimensional Planning and Virtual Radiographs in Revision Total Hip Arthroplasty for Instability", Clinical Orthopaedics and Related Research, No. 442, pp. 35-38, Jan. 2006.
Staudte et al. "Computer-Assisted Operation Planning and Technique in Orthopedics", North Rhine-Westphalia Acad. for Sciences, Lecture N.444, ISSN 0944-8799, 2000, 17 pages—In German.
Staudte et al. "Computer-Assisted Operation Planning and Technique in Orthopedics", North Rhine-Westphalia Acad. for Sciences, Lecture N.444, ISSN 0944-8799, 2000, 34 pages—English Translation.
Surgicad Design Combines 3-D Visualization with CAD Tools, Intergraph Corp. and Surgicad Corp. News Brief, 2 pages, Sep. 1993.
Thoma et al. "Custom-made knee endoprosthetics using subtraction data of three-dimensional CT scans—A new approach," Der Orthopäde, Springer-Verlag, vol. 29, No. 7, pp. 641-644, (Jul. 2000) (In German).
Thoma et al. "Custom-made knee endoprosthetics using subtraction data of three-dimensional CT scans—A new approach," Der Orthopäde, Springer-Verlag, vol. 29, No. 7, pp. 641-644, (Jul. 2000)(English Translation with Certification).
Thoma et al. "Use of a New Subtraction Procedure Based on Three-Dimensional CT Scans for the Individual Treatment of Bone Defects in the Hip and Knee," Journal DGPW, No. 17, pp. 27-28 (May 1999) (In German).
Thoma et al. "Use of a New Subtraction Procedure Based on Three-Dimensional CT Scans for the Individual Treatment of Bone Defects in the Hip and Knee," Journal DGPW, No. 17, pp. 27-28 (May 1999)(English Translation with Certification).
Wu et al. "Application of Laser Measuring, Numerical Simulation and Rapid Prototyping to Titanium Dental Castings", Dental Materials, vol. 17, pp. 102-108, 2001.

SOLID FREEFORM FABRICATION OF IMPLANT COMPONENTS

RELATED APPLICATIONS

This application is a divisional of U.S. application Ser. No. 14/033,095, entitled "Solid Freeform Fabrication of Adaptable Implant Components," filed Sep. 20, 2013, which in turn claims the benefit of U.S. Provisional Application No. 61/703,768, entitled "Solid Freeform Fabrication of Adaptable Implant Components" filed Sep. 20, 2012, and U.S. Provisional Application No. 61/801,992, entitled "Solid Freeform Fabrication of Adaptable Implant Components" filed Mar. 15, 2013. Each of the above-described applications is hereby incorporated herein by reference in its entirety.

TECHNICAL FIELD

The embodiments described herein relate to methods and systems for manufacturing implants, implant components and/or related tools using solid freeform fabrication or additive metals technologies, including SLM (selective laser melting). More specifically, embodiments described herein include implants incorporating porous features.

BACKGROUND

Recently, the joint replacement field has come to embrace the concept of "patient-specific" and "patient-engineered" implant systems. With such systems, the surgical implants, associated surgical tools and procedures are designed or otherwise modified to account for and accommodate the individual anatomy of the patient undergoing the surgical procedure. Such systems typically utilize non-invasive imaging data, taken of the individual pre-operatively, to guide the design and/or selection of the implant, surgical tools, and the planning of the surgical procedure itself. Because "patient-specific" and "patient-engineered" implant systems are created using anatomical information from a particular patient, such systems are generally created after the patient has been designated a "surgical candidate" and undergone non-invasive imaging.

DETAILED DESCRIPTION

Figure 1:
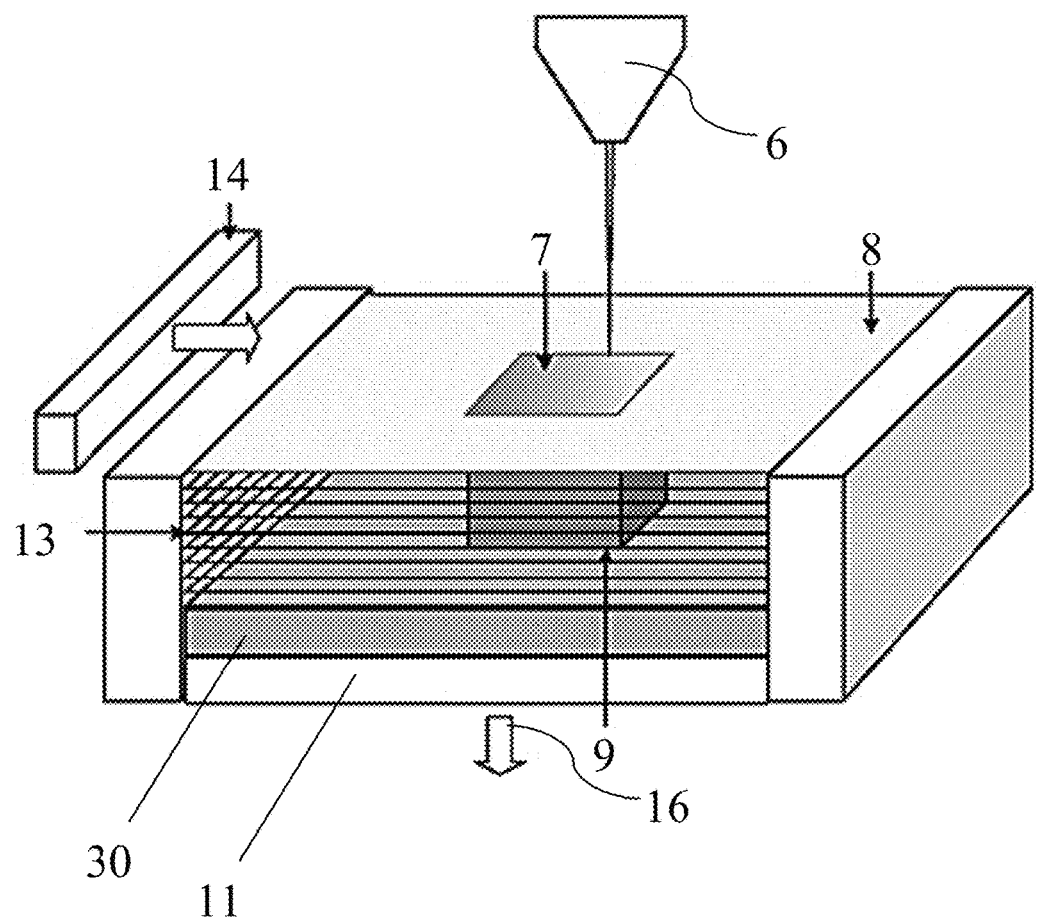
FIG. 1 depicts a schematic view of equipment and the process used in a typical SLM manufacturing process.

Solid Freeform Fabrication (SFF) includes a group of emerging technologies that have revolutionized product development and manufacturing. The common feature shared by these technologies is the ability to produce freeform, complex geometry components directly from a computer generated model. SFF processes generally rely on the concept of layerwise material addition in selected regions. A computer generated model serves as the basis for making a replica. The model is mathematically sliced and each slice is recreated in the material of choice to build a complete object. A typical SFF machine can be likened to a miniaturized "manufacturing plant" representing the convergence of mechanical, chemical, electrical, materials and computer engineering sciences.

Various of the embodiments described herein include advancements and improvements in or related to the use of SFF and Rapid Prototyping (RP) or "additive" manufacturing processes, including Selective Laser Sintering (SLS), Direct Metal Laser Sintering (DMLS), Electron Beam Melting (EBM) and Selective Laser Melting (SLM) techniques, in the design, selection, development, manufacturing and/or finishing of patient-specific and/or patient-engineered implant components.

While SFF can be used to manufacture a wide variety of object shapes, there are a host of perceived disadvantages and/or limitations associated with various of these techniques that have served to limit their widespread adoption. In the case of such additive manufacturing, these disadvantages can include implant components and/or tools that (1) can be limited in the range of potential implant materials, (2) often have a rough grainy and porous surface finish, (3) often experience high temperature gradients that can result in a build-up of thermal stresses, (4) typically experience a relatively large shrink rate that can cause the part (or portions thereof) to warp, bow or curl, (5) undergo a rapid solidification, often leading to the occurrence of segregation phenomena and the presence of non-equilibrium phases, (6) have a surface feature detail that is relatively coarse, and the object can have a surface roughness created by the layerwise building techniques (e.g., the "staircase effect"), (7) are to some extent dependent upon the stability, dimensions and behavior of the particle "melt pool," which can determine to a great extent the porosity and surface roughness, and (8) require specialized and relatively expensive equipment (e.g., the laser printing machinery and specially processed raw materials) for manufacture, as well as highly trained operators.

Typically, SFF manufacturing processes and techniques seek to minimize and/or eliminate the various inherent deficiencies or weaknesses, especially when final functional parts are being manufactured. However, in various embodiments disclosed herein, the controlled inclusion of manufacturing artifacts, such as various combinations of the "disadvantages" previously discussed, can facilitate the creation and/or manufacture of implant components that are particularly well suited for use in accommodating unanticipated intraoperative modifications. In many cases, SFF manufacturing processes can be employed to create patient-specific implants that are adaptable to a variety of surgical "options" presented to a surgeon, with one or more user-executed modifications to the implant component desirably altering the implant shape and/or performance to match the chosen surgical outcome.

Various embodiments, and the various SFF manufacturing techniques described herein, including SLS, DMLS, EBM or SLM manufacturing, may be utilized to create complex geometries and/or surfaces that can be employed for a variety of functions, which could include the creation of textured and/or porous-walled surfaces, including cement pockets and/or bony ingrowth surfaces, for securing the implant to the patient's underlying bone. Various shapes could include defined micro-cavities and/or micro-protrusions on and/or within the implant surface.

While patient-specific and/or patient-adapted/engineered implants have seen significantly increased adoption rates over the past decade, there are many situations where an implant created using patient-specific anatomical information may not be an optimal solution for the patient's surgical needs. While modular and one-size-fits all implants typically require significantly more bone and tissue removal than their patient-specific counterparts, the ability to stock and inventory a wide variety of such implant components and surgical tools in a modular system can provide a surgical flexibility that patient-specific implants may find difficult to match in a cost-effective manner. For example, if direct visualization of a patient's anatomy impels a surgeon to resect significantly more anatomical structure than was originally intended (based on earlier non-invasive imaging studies), a commensurate change to the desired implant shape and/or size necessitated by the altered resection might be fulfilled by choosing a different sized modular implant component from inventory. In a similar manner, if the local bone conditions are better than the surgeon originally anticipated from pre-operative images, the surgeon might choose to resect significantly less of the anatomical structures, and/or possibly opt for an alternative implant system (and/or component thereof) that utilizes bony-ingrowth surfaces, rather than relying on securement based on bone cement and/or other surgical materials.

Moreover, because a patient's anatomy is constantly remodeling and changing, as well as the ever-present potential for infection, dislocation, excessive wear and/or failure of implant components, many patients are forced to eventually undergo one or more revision surgeries to repair and/or replace a joint implant (and/or component thereof) that has become damaged, malfunctions and/or is unacceptably painful. In many cases, portions of the implant that are removed may still be securely attached to the underlying anatomy, and the removal of such components can involve unnecessary damage to the patient's anatomy that can further complicate the revision and/or healing process.

To alleviate, address and/or accommodate such concerns, various embodiments described herein include implant components that incorporate frangible links, deformable regions, surface textures and/or other features that facilitate and/or enable the intraoperative modification of patient-specific and/or patient-adapted implant components by surgical personnel. Features described herein, which can be specifically tailored to an individual anatomy, can facilitate the use of standard and/or readily available surgical tools to alter various implant features to accommodate modifications that may occur during the surgical procedure. Moreover, the various features can be manufactured as part of the initial manufacturing process, which may include creation of one or more implant components using Solid Freeform Fabrication methods, including via SLM.

Manufacturing Technologies

Various technologies appropriate for manufacturing implants and tools are known in the art, for example, as described in *Wohlers Report 2009, State of the Industry Annual Worldwide Progress Report on Additive Manufacturing*, Wohlers Associates, 2009 (ISBN 0-9754429-5-3), available from the web www.wohlersassociates.com; Pham and Dimov, *Rapid manufacturing*, Springer-Verlag, 2001 (ISBN 1-85233-360-X); Grenda, *Printing the Future, The 3D Printing and Rapid Prototyping Source Book*, Castle Island Co., 2009; *Virtual Prototyping & Bio Manufacturing in Medical Applications*, Bidanda and Bartolo (Eds.), Springer, Dec. 17, 2007 (ISBN: 10: 0387334297; 13: 978-0387334295); *Bio-Materials and Prototyping Applications in Medicine*, Bártolo and Bidanda (Eds.), Springer, Dec. 10, 2007 (ISBN: 10: 0387476822; 13: 978-0387476827); Liou, *Rapid Prototyping and Engineering Applications: A Toolbox for Prototype Development*, CRC, Sep. 26, 2007 (ISBN: 10: 0849334098; 13: 978-0849334092); *Advanced Manufacturing Technology for Medical Applications: Reverse Engineering, Software Conversion and Rapid Prototyping*, Gibson (Ed.), Wiley, January 2006 (ISBN: 10: 0470016884; 13: 978-0470016886); and Branner et al., "Coupled Field Simulation in Additive Layer Manufacturing," 3rd International Conference PMI, 2008.

Exemplary Techniques for Forming or Altering a Patient-Specific and/or Patient-Engineered Implant Component for a Patient's Anatomy

| Technique | Brief description of technique and related notes |
| --- | --- |
| CNC | CNC refers to computer numerically controlled (CNC) machine tools, a computer-driven technique, e.g., computer-code instructions, in which machine tools are driven by one or more computers. Embodiments of this method can interface with CAD software to streamline the automated design and manufacturing process. |
| CAM | CAM refers to computer-aided manufacturing (CAM) and can be used to describe the use of software programming tools to efficiently manage manufacturing and production of products and prototypes. CAM can be used with CAD to generate CNC code for manufacturing three-dimensional objects. |
| Casting, including casting using rapid prototyped casting patterns | Casting is a manufacturing technique that employs a mold. Typically, a mold includes the negative of the desired shape of a product. A liquid material is poured into the mold and allowed to cure, for example, with time, cooling, and/or with the addition of a solidifying agent. The resulting solid material or casting can be worked subsequently, for example, by sanding or bonding to another casting to generate a final product. |
| Welding | Welding is a manufacturing technique in which two components are fused together at one or more locations. In certain embodiments, the component joining surfaces include metal or thermoplastic and heat is administered as part of the fusion technique. |
| Forging | Forging is a manufacturing technique in which a product or component, typically a metal, is shaped, typically by heating and applying force. |
| Rapid prototyping | Rapid prototyping refers generally to automated construction of a prototype or product, typically using an additive manufacturing technology, such as EBM, SLS, SLM, SLA, DMLS, 3DP, FDM and other technologies |
| EBM ® | EBM ® refers to electron beam melting (EBM ®), which is a powder-based additive manufacturing technology. Typically, successive layers of metal powder are deposited and melted with an electron beam in a vacuum. |
| SLS | SLS refers to selective laser sintering (SLS), which is a powder-based additive manufacturing technology. |

-continued

| Technique | Brief description of technique and related notes |
|---|---|
| | Typically, successive layers of a powder (e.g., polymer, metal, sand, or other material) are deposited and melted with a scanning laser, for example, a carbon dioxide laser. |
| SLM | SLM refers to selective laser melting ™ (SLM), which is a technology similar to SLS; however, with SLM the powder material is fully melted to form a fully-dense product. |
| SLA or SL | SLA or SL refers to stereolithography (SLA or SL), which is a liquid-based additive manufacturing technology. Typically, successive layers of a liquid resin are exposed to a curing, for example, with UV laser light, to solidify each layer and bond it to the layer below. This technology typically requires the additional and removal of support structures when creating particular geometries. |
| DMLS | DMLS refers to direct metal laser sintering (DMLS), which is a powder-based additive manufacturing technology. Typically, metal powder is deposited and melted locally using a fiber optic laser. Complex and highly accurate geometries can be produced with this technology. This technology supports net-shaping, which means that the product generated from the technology requires little or no subsequent surface finishing. |
| LC | LC refers to LaserCusing ®(LC), which is a powder-based additive manufacturing technology. LC is similar to DMLS; however, with LC a high-energy laser is used to completely melt the powder, thereby creating a fully-dense product. |
| 3DP | 3DP refers to three-dimensional printing (3DP), which is a high-speed additive manufacturing technology that can deposit various types of materials in powder, liquid, or granular form in a printer-like fashion. Deposited layers can be cured layer by layer or, alternatively, for granular deposition, an intervening adhesive step can be used to secure layered granules together in bed of granules and the multiple layers subsequently can be cured together, for example, with laser or light curing. |
| LENS | LENS ® refers to Laser Engineered Net Shaping ™ (LENS ®), which is a powder-based additive manufacturing technology. Typically, a metal powder is supplied to the focus of the laser beam at a deposition head. The laser beam melts the powder as it is applied, in raster fashion. The process continues layer by and layer and requires no subsequent curing. This technology supports net-shaping, which means that the product generated from the technology requires little or no subsequent surface finishing. |
| FDM | FDM refers to fused deposition modeling ™ (FDM) is an extrusion-based additive manufacturing technology. Typically, beads of heated extruded polymers are deposited row by row and layer by layer. The beads harden as the extruded polymer cools. |

Patient-specific and/or patient-engineered implants can be produced using 3-dimensional printing technology (also known as Solid Freeform Fabrication or "SFF") to create solid, physical implant components from an electronic or computerized data file (e.g., a CAD file). 3D printing techniques such as Selective Laser Sintering (SLS), EBM (Electron Beam Melting) and Selective Laser Melting (SLM—also known as Direct Metal Laser Sintering—DMLS—or LaserCusing) can allow the creation of durable metallic objects that are biocompatible and can directly serve as implant components.

In certain embodiments, an implant can include components and/or implant component parts produced via various methods. For example, in certain embodiments for a knee implant, the knee implant can include a metal femoral implant component produced by casting or by an additive manufacturing technique and having a patient-specific femoral intercondylar distance; a tibial component cut from a blank and machined to be patient-specific for the perimeter of the patient's cut tibia; and a tibial insert having a standard lock and a top surface that is patient-specific for at least the patient's intercondylar distance between the tibial insert dishes to accommodate the patient-specific femoral intercondylar distance of the femoral implant.

As another example, in certain embodiments a knee implant can include a metal femoral implant component produced by casting or by an additive manufacturing technique that is patient-specific with respect to a particular patient's M-L dimension and standard with respect to the patient's femoral intercondylar distance; a tibial component cut from a blank and machined to be patient-specific for the perimeter of the patient's cut tibia; and a tibial insert having a standard lock and a top surface that includes a standard intercondylar distance between the tibial insert dishes to accommodate the standard femoral intercondylar distance of the femoral implant.

The steps of designing an implant component and associated methods of SFF manufacturing such objects using additive material technologies such as SLS, SLM, EBM and/or SLS, as described herein, can include both configuring one or more features, measurements, and/or dimensions of the implant (e.g., derived from patient-specific data from a particular patient and adapted for the particular patient), manufacturing and finishing the implant. In certain embodiments, manufacturing can include making the implant component from starting materials, for example, metals and/or polymers or other materials in solid (e.g., powders or blocks) or liquid form In various embodiments, the design of an implant component or other manufactured object may be altered or modified to accommodate advantages and/or limitations of a specific manufacturing process, such as DMLS or SLM, which may result in differing designs for a single anatomical situation (i.e., for a single patient anatomy) based on differing manufacturing methods. The various design changes, which can (but not necessarily must) have varying degrees of impact on the ultimate performance and/or reliability of the implant, can be incorporated to accommodate a wide variety of considerations, including tolerancing and dimensioning limitations of specific manufacturing methodologies and/or equipment, design limitations and/or object feature (e.g., surface and/or subsurface feature) orientation and/or shape requirements.

SLM Manufacturing

FIG. 1 depicts a schematic view of equipment and the process used in a typical SLM manufacturing process. SLM is a powder bed 8 process that begins with the deposition of a thin layer of powder onto a substrate 30, which can be disposed on a processing table 11. A high power laser 6 scans the surface of the powder, generating heat that causes the powder particles to melt (see melted powder 7) and form a melt pool which solidifies as a consolidated layer of material. Once the layer has been scanned and relevant portions melted/solidified, another layer of powder is deposited, which is then subsequently scanned and melted/solidified to form the next layer of the part. This process continues with multiple layers 13 until enough layers of material have been deposited/melted/solidified to create a desired object 9. Powder particles that are not melted remain loose and are removed (and can typically be reused) once the component is complete.

In various additional embodiments, SLM manufacturing processes can be employed in the design and/or manufacture of implant components having intentional "defects" or frangible features, deformable regions and/or other planned internal/external attributes that facilitate the revision and/or removal of implant components and/or portions thereof during primary and/or revision surgical procedures. Such implants can include planned areas of increased porosity and/or localized lines of weakness that present reduced resistance to surgical cutting, drilling, impaction and/or other tools, as well as implant portions that facilitate modification, deformation, bending and/or work-hardening (and subsequent fracture, if desired) of various component features and/or portions thereof. In various embodiments, the planned features may facilitate the complete and/or partial removal of implant components, with the partial removal of implant portions potentially facilitating surgical access to implant pieces still remaining in contact with and/or secured to the patient's anatomy. In alternative embodiments, various portions of implant components may remain permanently anchored and/or otherwise connected to the patient's anatomy, and may be ignored and/or utilized for securement of revision implant components.

Creation of Pre-Defined Weakness Regions

Unlike traditional manufacturing methods such as casting and/or machining, SFF layer-wise manufacturing techniques provide an exceptional level of design and manufacturing access to the internal structure(s) of a manufactured part. Because SFF provides a significant level of control or "tailoring" of the micro and macroscopic internal and external structures of manufactured objects, the techniques of laser track scanning and melt pool layering can be particularly useful in the manufacture of adaptable orthopedic implant components. In various embodiments, implant components manufactured using SFF techniques can include a variety of internal and external structures, which can be formed in a single manufacturing operation, if desired. For example, some portion of an implant component formed using SFF technology could have a relatively smooth, uniform and continuous external layer, while incorporating a less continuous or "disrupted" internal region in selected areas. Depending upon the design of implant features as well as the location and distribution of disrupted regions, various portions of the implant may be sensitive or otherwise susceptible to specific and/or unusual loading modalities, which could be employed to selectively separate, flex, bend, fracture and/or otherwise modify portions of the implant.

The use of rapid prototyping techniques to fabricate both the implant and disrupted region(s) is advantageous because it provides the ability to modify internal structural features of the implant in a desired manner while retaining a smooth, continuous external surface (where such a surface is desired). Other known fabrication methods, such as casting, machining and/or thermoforming, fully surround the implant with a matrix material to form the shape of the implant, and thus internal structural features of the implant are generally uniform to the surface of the implant. The present disclosure provides a designer with the ability to provide a high level of mechanical support for component retention (e.g., functional anchor pegs) where peg removal is not desired, as well as rapid and easy disengagement of the peg from the implant body if such removal is warranted.

Frangible Links and Removable Guides

Figure 2A:
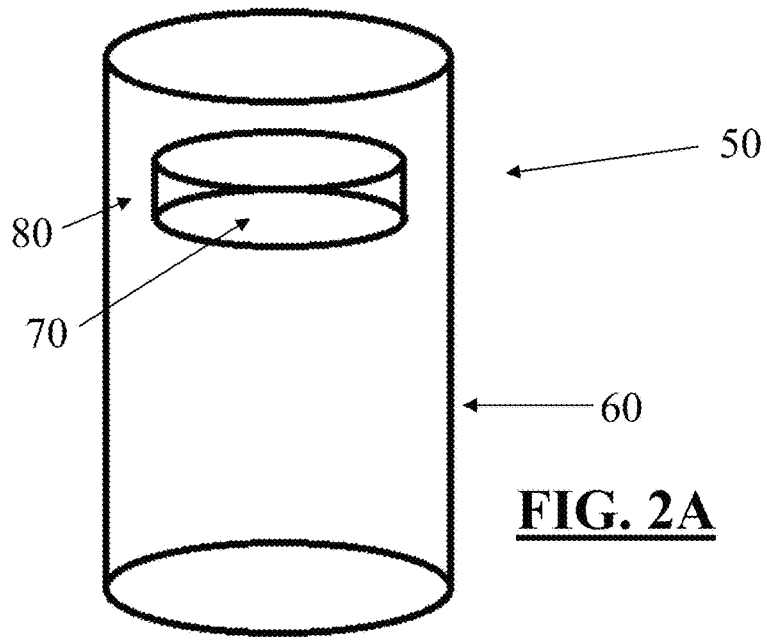
FIG. 2A depicts a perspective view of a frangible portion or link to facilitate separation of an implant component portion at a predetermined location.
Figure 2B:
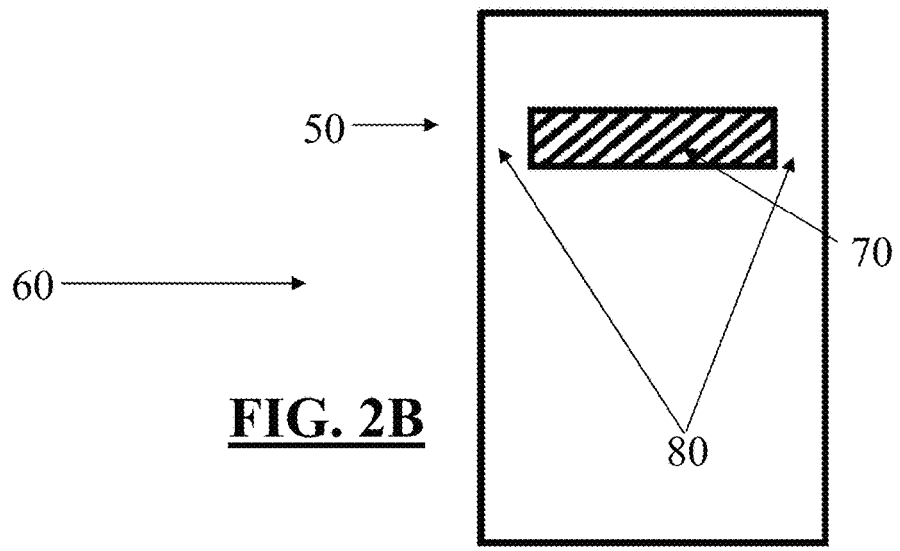
FIG. 2B depicts a side plan view of the frangible link of FIG. 2A.

In various embodiments, an adaptable feature could include a frangible portion or link that facilitates separation of an implant component portion at a predetermined location. One embodiment of such a frangible link is shown in FIGS. 2A and 2B, which are perspective and side plan views, respectively, of a frangible portion 50 formed in an anchor peg body 60 to allow the peg to be frangibly separated from the implant body (not shown). The frangible portion 50 can be formed at various locations along the peg and/or within the body, but in the embodiment shown the frangible portion 50 can be located adjacent where the anchor peg meets the implant body. The frangible portion 50 can include a central section 70 and an outer wall section 80, which as shown surrounds the central section 70 and forms a continuous outer surface with the remainder of the peg body 60. The central section 70 is formed during the SFF manufacturing processes to have a significantly weaker structure than the surrounding peg material, including the outer wall section. This central structure, which in various embodiments could comprise a void, a highly porous structure, a loosely interconnected structure and/or a cavity partially or completely filled with virgin powder material (i.e., unheated powder material), all of which can be created as a portion of the peg and/or implant during the SFF manufacturing process. In one exemplary embodiment, the central structure could be formed using a SLM layering technique, with the melt pool creating the outer wall section 80 in a typical manner, and the design plan causing the control apparatus to avoid laser contact with the powder in the central structure. In one alternative embodiment, the outer wall section could the formed using a SLM layering technique with the laser, and then using significantly less or more laser energy impacting on the material in the central section, which could weakly bond the material (less energy) and/or vaporize and "bubble" the material (more energy), creating a highly porous and significantly weaker central section.

Depending upon the material strength as well as the thickness of the outer wall portion (and somewhat dependent upon the strength of the central layer), the frangible portion 50 can be designed and adapted to break when a predetermined force and/or force vector(s) is/are applied to the peg, thereby allowing at least a portion of the peg to be separated from the implant body. In this manner, a portion of the implant can be designed to fracture and/or bend at a known location and/or under a known force without requiring alteration of the surface characteristics of the implant.

In addition to the various methods of controlling internal implant structures using SFF techniques described herein, a variety of physical design techniques could be used to augment the frangible portion, which could include a reduced diameter region or thinned region of material formed between the peg and the implant body. Other configurations for the frangible portion could include webbing, forming of an annular grooved in an outer surface of the peg, or other techniques known in the art. In various alternative embodiments, internal geometric features could be designed into the central cavity, such as geometry that limits and/or increases notch sensitivity or weakness/strength of the material, depending upon the desired outcome.

A variety of materials, including both plastics and metals, could be used for the implant and/or the post and/or the frangible portion, although the frangible portion in various embodiments will preferably be formed of the same material as the implant body. In use, the frangible portion can be designed to provide a weak spot in the anchor peg that allows the anchor peg to be easily separated from the implant body when a predetermined force is applied thereto.

Figure 3A:
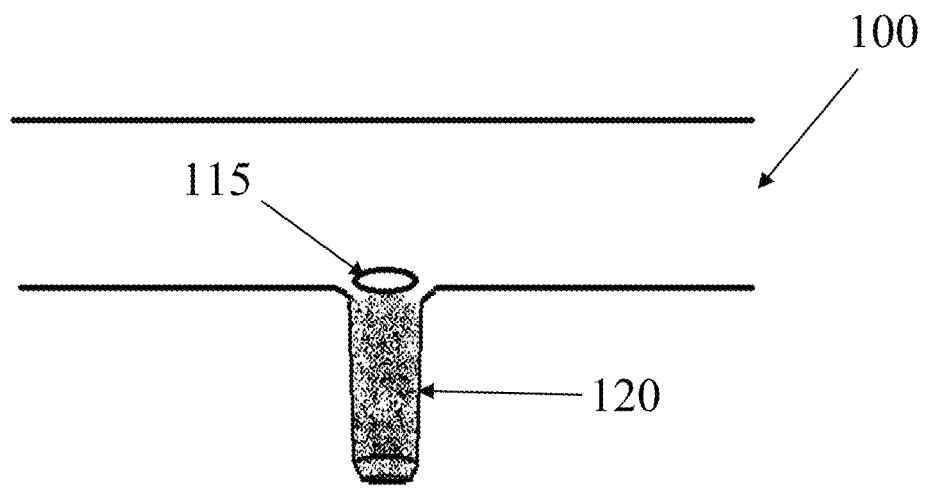
FIG. 3A depicts a partial view of a frangible portion formed internally within an implant body.
Figure 3B:
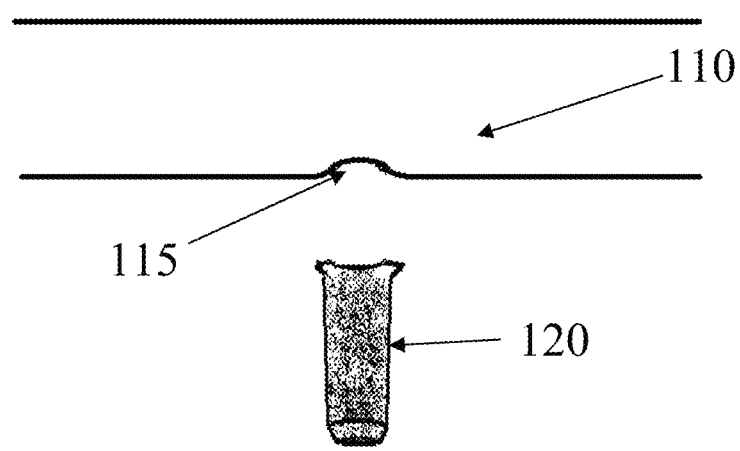
FIG. 3B depicts the frangible portion of FIG. 3A separated.

In various alternative embodiments, the frangible portion could be formed internally within the implant body. For example, in the embodiment of FIG. 3A, an implant body 100 has been formed using SFF manufacturing techniques with a frangible portion 110 including a void 115 or other manufactured artifact positioned adjacent an anchoring peg 120. If removal of the peg 120 is desired by operating room personnel, the peg 120 can be separated from the implant body 100 by the application of sufficient force (see FIG. 3B). In various embodiments, the removal of the peg can leave a relatively smooth implant surface and/or a small depression, with little or no material projection out of the implant surface to impede implantation of the non-modified implant (without the peg). If desired, the void 115 could comprise a porous or other material that is exposed to the surface of the implant when the peg is removed. This material could facilitate bony ingrowth or adhesion of bone cement, if desired. In alternative embodiments, the void could be used for attachment to the anatomical structures (e.g., as a securement hole for orthopedic screws, etc.) or as a connection point for additional implant components.

In various embodiments, an anchoring peg for a femoral implant component (or other implant feature) could include a frangible feature proximate an implant attachment location. The anchor could comprise a cylindrical protrusion extending from a bone-facing portion of the implant, which desirably secures within a bore formed in the underlying anatomical structure, thereby securing the implant to the bone. Structurally, the anchor could comprise a cylindrical body, the majority of which comprises a solid, essentially uniform CrCo formed by a SLM manufacturing process. However, at a location proximate the implant, at least one or more layers of the anchor could comprise a generally cylindrical exterior of relatively solid CrCo encasing a cylindrical internal portion comprising a generally disrupted material, with the interior forming a preferred fracture zone. In use, if detachment of the anchor from the implant is desired for any reason, a surgical wrench or other device could be used to grasp and rotate the anchor in a clockwise or counterclockwise direction. The rotational motion would desirably impart sufficient stress on the thin cylindrical base region proximate the disrupted interior portion (with the interior portion desirably providing little or no resistance to the rotation), thereby allowing the thin outer wall to fracture and the anchor to detach from the implant. The implant could then be utilized in the standard manner without the cylindrical anchor attached.

In contrast, if use of the implant with the attached anchor was desired, the combination of the thin cylindrical wall surrounding the disrupted interior region would desirably provide sufficient support to withstand any expected flexion and/or tension/compression forces experience during normal anatomical loading conditions. By creating a detachable portion that remains attached during expected loading conditions, but that can be fractured, removed and/or otherwise modified by application of unexpected forces at a surgeon's option, various embodiments described herein grant the surgeon with an unusual degree of flexibility in accommodating intraoperative modifications to the surgical procedure and/or implant components.

In another exemplary embodiment, an implant could include a removable portion that can be removed and/or otherwise altered to change the shape and/or size of the implant. For example, a femoral implant component could include a trochlear plate that extends the trochlear groove a desired distance towards and/or into the intercondylar notch. Such a plate structure might be desired to prevent the natural patella from dislocating and/or dropping into the intercondylar notch after replacement of one or more femoral surfaces. However, if intraoperative conditions dictate an unexpected repair to the patient's patella, an artificial patellar implant portion may not require and/or desire the presence of the trochlear plate. In such a case, the plate could be removed by grasping the plate portion with surgical pliers and rotating the plate relative to the implant, which desirably fractures and/or otherwise removes the plate structure without damaging or affecting any of the external articulating structures of the femoral implant.

Removable/Bendable Mating Features

Various embodiments of patient-specific implants described herein can include adaptable mating features for integrating with other orthopedic implant components. The adaptable mating features could include protrusions, flanges, blades, hooks, plates, openings, depressions and/or other attachment sites that can be selectively modified and/or removed by a user. In various embodiments, such features could be integrated into knee and/or hip implant components, including an acetabular shell for a hip implant, that could be configured to couple with an augment, flange cup, mounting member and/or any other suitable orthopedic attachment, as well as various combinations thereof.

For example, various embodiments of an adaptable feature could comprise one or more flanges or mounting members designed and manufactured via SFF techniques to be permanently fixed to an implant component. Desirably, the flanges could include "disrupted" regions comprising frangible portions that allow for selective detachment between the implant body and a connection region, such as screw holes or other structures for receiving fasteners. In various embodiments, the frangible portions could incorporate reduced cross-sectional areas (in addition to or in place of deliberate disrupted regions, as described herein) that allow bending or breaking or cutting of the flange without disturbing the geometry of the implant body. If desired, selective portions of a given flange could be similarly designed, to allow removal of a portion of the flange while leaving a remaining portion of the flange connected to the implant body. Further, there may be more than one level of frangibility on a given flange (and/or between flanges) to compensate for different surgical appliances and vertical, horizontal and/or radial adjustability of the placement, as well as to reduce inadvertent fracture of the wrong frangible link when multiple such links are present. In various embodiments, the frangible portions could include physical pre-stressing or otherwise be pretreated to make the frangible portions weaker than other areas of the mounting members.

Depending upon the intended application, one or more porous pieces or surfaces could be designed for a patient-specific implant and provided on adaptable or bendable mounting members such as bendable flanges or plates, or any other mounting arrangement. The mounting arrangement could be modular, attachable, or integrally-provided. The bendable region(s) could include "disrupted" regions, as described herein, specifically designed and structured during SFF formation to allow deformation of the mounting arrangement. Such bendable regions could include porous or bony ingrowth surfaces, the locations of which could be modified by the surgeon in-situ to be positioned proximate to bleeding bone or other anatomy.

In various alternative embodiments, adaptable and/or porous features may be incorporated into an implant to reduce, by a certain degree, the stiffness and/or rigidity of an implant or anchoring component while maintaining a desired degree of strength. Such features may facilitate the intra-operative modification of implant features (e.g., bending of an anchoring peg in a desired manner by operating room personnel) as well as potentially reduce the opportunity for fatigue or "work-hardening" fracture of implant components or support structures thereof.

Manufacturing Biofunctional and/or Porous Regions

In various embodiments, SFF manufacture of implant components (e.g., SLM, SLS, DMLS techniques) can be used to create biofunctional implant structures and/or surfaces (and/or securement features), which may be particularized for an individual patient and/or surgical procedure. Such surfaces can be designed and utilized to achieve a wide variety of functional objectives, from creating osteo-inductive and/or osteo-conductive surfaces that desirably promote bony ingrowth to porous surfaces to promote bone cement adhesion (as well as relatively smooth surfaces that desirably inhibit bony and/or soft tissue adhesion). Utilizing SFF manufacturing to form implant structures with selectively varying bone ingrowth and/or fixation properties can permit manufacturing implant features with highly individualized and optimized, patient-adapted fixation characteristics.

In various embodiments, exemplary porous coating parameters that can be varied based on patient-specific information can include, for example, the locations on/in implant components where porous coating is used and/or features specific to the coating itself. For example, in some embodiments, SLM manufacturing can be used to create an implant feature with a uniform internal microstructure (to desirably promote implant strength and/or durability) in combination with a roughened and/or porous surface structure that, depending upon a variety of manufacturing parameters, can be particularized for a wide variety of surgical objectives. For example, an outer implant surface can be created having an optimal and/or designed pore size for promoting bone ingrowth in a certain patient population. As another example, an implant outer surface can be created having a designed pore size and/or surface roughness for promoting bone cement attachment and/or adhesion. Where patient-specific information indicates a preferred microstructure and/or macrostructure for the implant or portions thereof, implant modeling and SFF fabrication techniques can be employed to create a unique implant.

In various embodiments, structures and/or surfaces of an implant can selectively be porous, roughened, smooth and/or hardened. As used herein, "porous" can generally be used to describe any portion of structure having a plurality of holes, spaces, gaps, channels, etc. therein. In some instances, a porous portion can consist of a plurality of small discrete particles of material (e.g., metal) that were bonded together at their points of contact with each other to define a plurality of connected interstitial pores. In other embodiments, a porous portion can consist of an organized lattice, mesh, and/or grid of material having multiple channels, spaces, and/or pores therein. The structural nature of a porous portion can be controlled by the design and/or manufacturing parameters provided to, as well the capabilities of, the SFF manufacturing equipment and process(es). In addition to altering physical characteristics by modifying the structural design and/or process parameters such as scanning speed, temperature, atmosphere and/or laser power, the various surface features created by the SLM manufacturing process could be dependent upon a wide variety of variables, including the grain size, shape and/or distribution (e.g., uniformity and/or nonuniformity) of the raw material, which may be particularized for a specific application and/or implant feature desired.

In various embodiments, various of the surface features of a patient-specific implant could be particularized to accommodate a variety of objectives, including various combinations of the following: (1) Smooth surfaces; (2) hardened surfaces; (3) porous surfaces for promoting bone infiltration and/or ingrowth; (4) roughened and/or porous surfaces for promoting material adhesion such as bone cement securement; and/or (5) porous surfaces for containing osteo-inductive agents and/or medicaments.

In various exemplary embodiments, a tibial implant could include one or more bone-facing surfaces that include specifically designed and manufactured porous surface features that promoted bone in-growth. Such porous features can be created in bone-facing portions of the implant (e.g., on one or more inner, bone facing surfaces and/or on the surface of impaction pegs, stems, pins and/or anchors, etc.) at locations where the intended surgical procedure is expected to create bleeding bone. At other locations on the implant, non-porous surface features may be created, such as along articulating and/or peripheral edge surfaces that are not expected to encounter bleeding bone and/or where bone ingrowth is not desired. In still other portions of the implant, if desired, other surface features may be incorporated, such as smooth and/or thickened surfaces where FEA or other analysis indicates the implant may experience increased and/or excessive stresses (e.g., thinned implant sections and/or notch sensitive locations, etc.). Still other portions of the implant may incorporate roughened and/or porous surfaces to accommodate bone cement and/or medications, if desired.

In at least one exemplary embodiment, one or more porous surfaces or other surface features can be designed into certain subregions of an implant component that interface with bone. In various alternative embodiments, such an implant can include some bone-interfacing subregions, with other subregions designed to mate with cement or other securement materials, thereby creating a patient-specific hybrid cemented/porous-coated implant.

In one alternative embodiment, a patient-specific implant component could include porous coatings on pegs or other anchor regions of the implant, with non-porous coatings (and/or coatings to facilitate securement by bone cement) on other bone-facing surfaces of the implant. Alternatively, a patient-specific implant component could include non-porous peg and/or anchor surface, with porous coatings on other bone-facing surfaces of the implant.

If desired, an implant can be designed and/or manufactured to include one or more porous regions that partially and/or completely extend through portions of the implant body. For example, a tibial tray may include one or more porous regions of the implant that extend completely through the tray body (from caudal to cephalad surfaces of the implant, for example), thereby allowing bone to grow completely through the implant, if desired. Such porous regions could be surrounded partially and/or completely by non-porous regions, such as a non-porous periphery of a tibial tray surrounding one or more porous regions formed centrally or in medial and lateral compartments of the tibial tray. If desired, such embodiments could allow for bone ingrowth completely through the metallic tray and into contact with a polymer, ceramic and/or metallic tray insert. In a similar manner, tibial alignment and/or securement fins could be partially and/or completely porous.

The inclusion of porous features is similarly contemplated with other joint implant components. For example, a central pin for securing a hip resurfacing implant could include one or more porous sections (or be completely porous), if desired.

If desired, an articular surface repair system can be affixed to subchondral bone, with one or more stems, or pegs, extending through the subchondral plate into the marrow space. In certain instances, this design can reduce the likelihood that the implant will settle deeper into the joint over time by resting portions of the implant against the subchondral bone. The stems, or pegs, can be of any shape suitable to perform the function of anchoring the device to the bone. For example, the pegs can be cylindrical or conical. Optionally, the stems, or pegs, can further include notches or openings to allow bone in-growth. In addition, the stems can be porous coated for bone in-growth.

In various embodiments, the adaptive features described herein can be applied to implant components for use with any joint including, without limitation, a spine, spinal articulations, an intervertebral disk, a facet joint, a shoulder, an elbow, a wrist, a hand, a finger, a hip, a knee, an ankle, a foot, or a toe joint. Furthermore, various embodiments described herein can encompass and/or apply to the design, selection and/or manufacture of standard and/or modular implants and/or implant components, if such are appropriate to a given patient's anatomy, as well as associated guide tools.

Improved Revisability

In various alternative embodiments, SLM manufacturing techniques can be employed to design and manufacture implant components having adaptable features that desirably improve and/or simplify a surgeon's ability to perform a subsequent revision surgery. Revision of an implant component may be indicated for a host of reasons, including implant fracture and/or failure, excessive wear, infection and/or excessive pain. In many revision cases, however, portions of an implant requiring revision may still remain anchored or otherwise secured to underlying portions of the patient's anatomy. In extreme cases, the removal of an implant component may necessitate significant resection of the patient's anatomy, which leaves significantly less of the native anatomical structures remaining for fixation of the revision component(s).

Figure 10A:
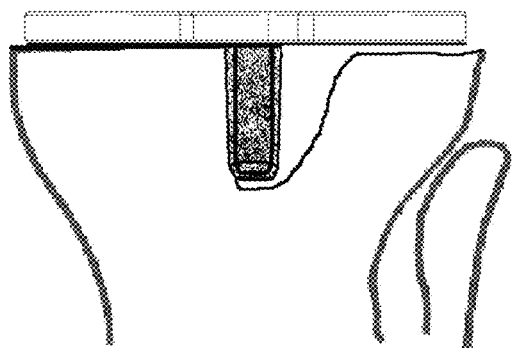
FIGS. 10A through 10C depict exemplary surgical steps for removing an implant without a frangible portion or other revision feature.
Figure 10B:
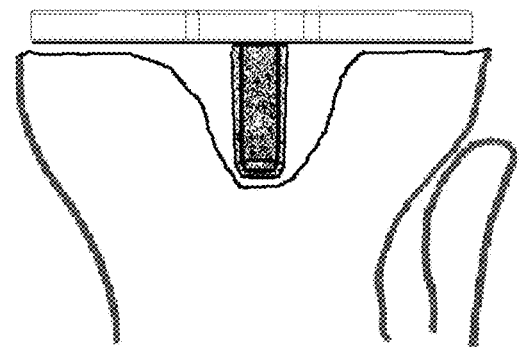
Figure 10C:
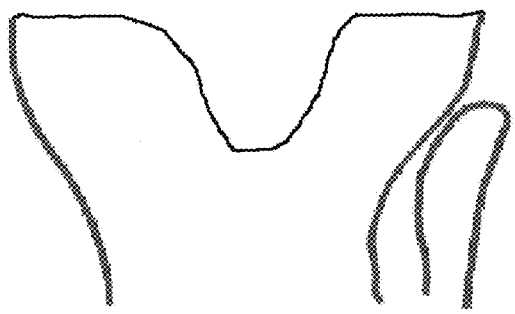

Traditionally, an implant component that was partially and/or fully-secured to the underlying anatomy (but which needed to be removed for some reason) could be difficult to separate from the patient's anatomy. In the case of a tibial tray implant having a centrally secured post, it might be necessary for a surgeon to cut around the existing implant or otherwise position instrumentation around the implant to loosen it from the surrounding bone and/or other anatomy prior to removal. In some instances, especially where the tray included a tibial keel or other rotation-resistant structures, it could be difficult to cut around the keel or otherwise access various areas of the bone-implant interface to loosen the implant. It might be particularly difficult to access certain areas of the implant depending upon the chosen access type and/or path(s). For example, if a medial/lateral surgical access path were chosen, the keel structure could impede access to posterior/lateral portions of the bone-implant interface. Accordingly, a surgeon might need to remove a significant amount of bone to separate the implant from the tibia, as well as remove significant bone to facilitate access to inner portions of the implant and/or surrounding the central post (see FIGS. 10A through 10C, for example). These difficulties would be exacerbated by the lack of access to such support structures, which necessitated significant bone removal for access to underlying structures, especially where the implant attachment was well secured. Moreover, where complete separation between the implant and the underlying bone was unsuccessful, subsequent removal of the implant could involve considerable force and/or inadvertently and undesirably fracture additional portions of the remaining anatomy.

To address various concerns, including those previously described, in various embodiments implant components can be designed and manufactured with features that facilitate revision of the component(s), should a subsequent revision of the implant become necessary. In various embodiments, implant features can include frangible and/or deformable sections that desirably withstand normal loading, but which are especially susceptible to specific loading modalities and/or modification by surgical tools, allowing portions and/or the entirety of the implant to be "released" and/or removed with little or no need for resection, modification and/or damage to the patient's underlying native anatomy. In various embodiments, the implant component can be provided with guiding features that facilitate the use of surgical tools to release portions of the implant, including the use of guide tools or jigs that incorporate implant-specific and/or anatomy-specific surfaces (of combinations thereof) to guide surgical tools.

Figure 4:
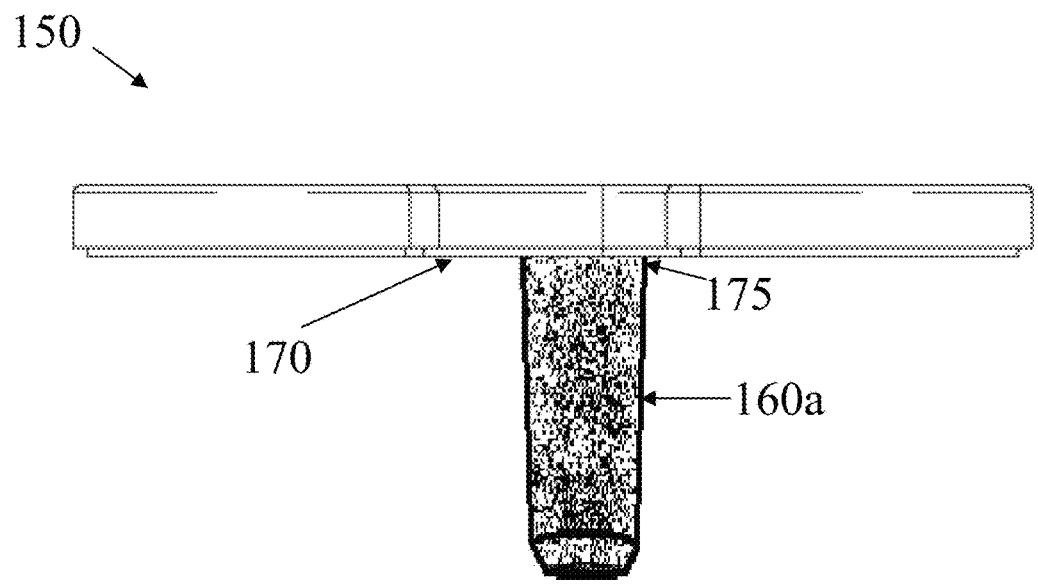
FIG. 4 depicts a side plan view of one exemplary embodiment of tibial tray implant.

In one exemplary embodiment shown in FIG. 4, a tibial implant component 150 can include a centrally-located anchoring peg 160a secured to a bone-facing side 170 of the implant. The peg could comprise a generally cylindrical body made of powdered and laser-melted CrCo, which can be produced using a SLM manufacturing method as previously described (e.g., as part of the implant manufacturing process via SLM). All or at least a portion of the peg can comprise a porous structure, as discussed herein, to facilitation bone ingrowth and fixation. Additionally or alternatively, a base portion 175 of the anchoring peg proximate the implant surface can include an adaptable feature that may include a region of significantly increased porosity (which may or may not extend to the surface of the peg, at the designer's option) and/or a significantly reduced material strength. Desirably, the base portion 175 does not appreciably affect the strength or durability of the peg as an anchoring feature (or at least does not reduce peg strength below an acceptable minimal functional level to properly function as an implant anchor), but the porous region will significantly reduce the resistance of the peg base to cutting tools such as vibratory saws and/or drills.

Figure 11:
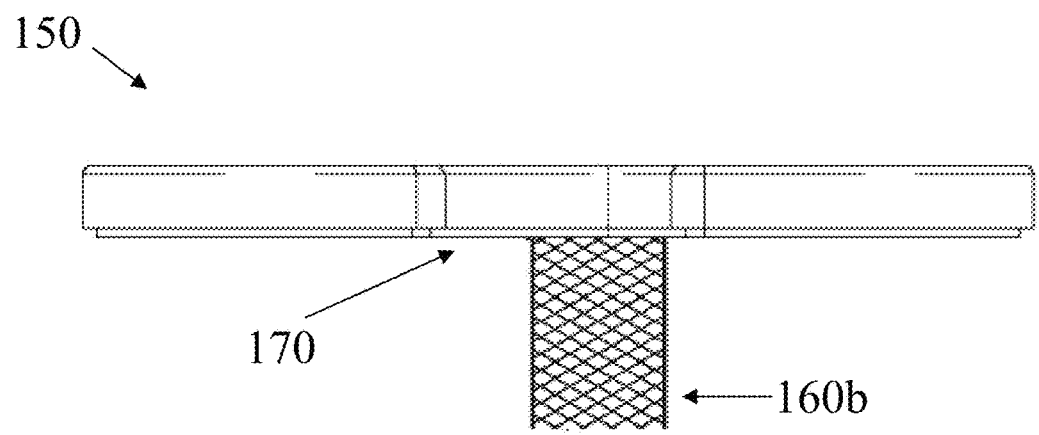
FIG. 11 depicts a side plan view of an exemplary embodiment of tibial tray including a peg comprising a mesh structure.

Similarly, in some embodiments, a tibial implant component 150 can be manufactured with a peg 160b formed, at least in part, of a lattice structure, as shown in FIG. 11. The lattice structure can comprise a plurality of organized individual filaments with openings between parallel filaments. The lattice structure can form a general outer periphery configured in, for example, a cylindrical shape, similar to that of peg 160a. As with other porous structures described herein, the openings in the lattice structure can provide for bone ingrowth. Furthermore, in some embodiments, the structure of the lattice (including, e.g., the filament width, spacing between filaments, angle of filaments, interconnections between filaments) can be designed, engineered, and/or otherwise optimized to patient-specific and/or design parameters. In some embodiments, a lattice structure, as opposed to other porous structures, may be advantageous for providing a desired strength or durability of the peg as an anchoring feature (or at least does not reduce peg strength below an acceptable minimal functional level to properly function as an implant anchor), while utilizing individual filaments of relatively small diameter. Such a configuration, with small diameter filament may permit a substantial amount of bone ingrowth between individual filaments, thereby enhancing fixation. And furthermore, the small diameter of individual filaments may particularly facilitate detachment of the tibial tray from the peg during a revision surgery. For example, at a time when the peg must be cut from the tray, a saw or other cutting tool may be applied with, e.g., only the force needed to cut a single filament at a time, in order to cut through the lattice structure of the peg. This amount of force to cut through a single filament may be substantially smaller than, for example, the amount of force required to cut through a peg of comparable diameter that is formed of a solid (or possibly other porous) structure.

Figure 5A:
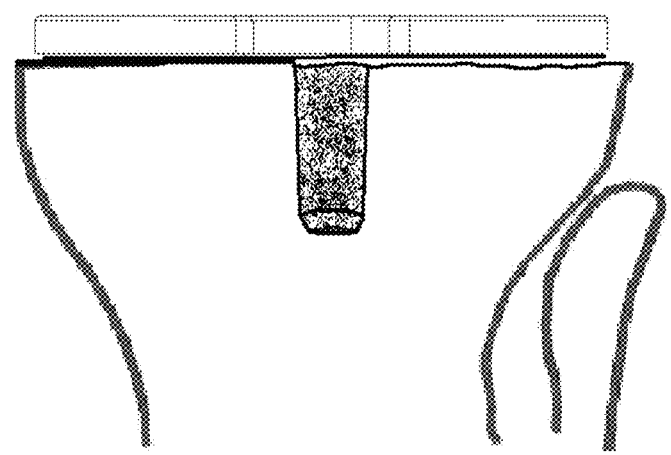
FIGS. 5A through 5E depict exemplary surgical steps for removing the implant of FIG. 4 from a patient's anatomy.
Figure 5B:
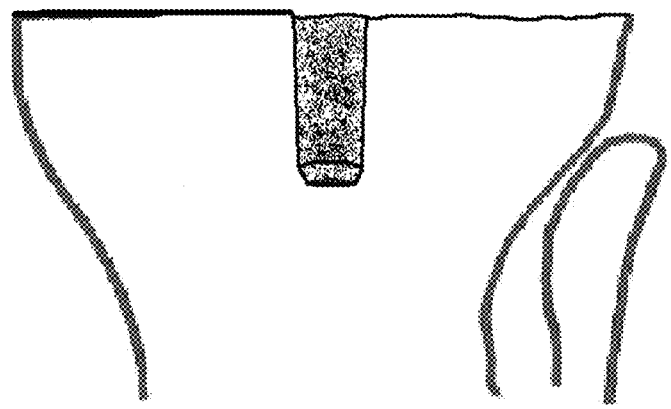
Figure 5C:
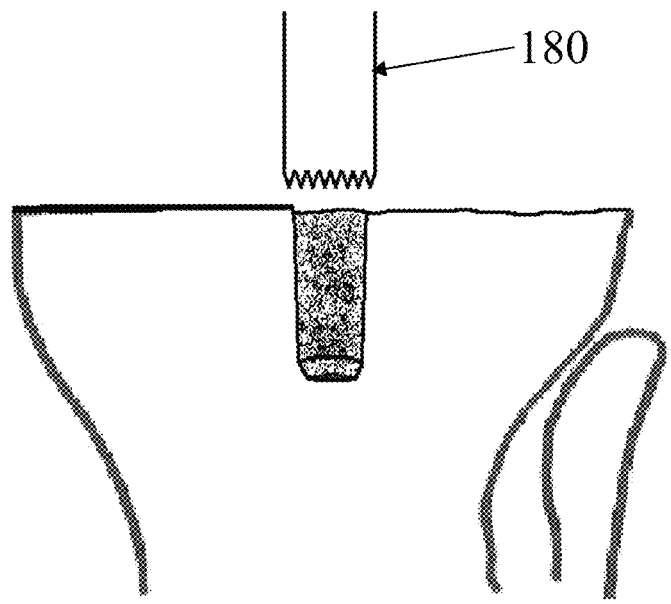
Figure 5D:
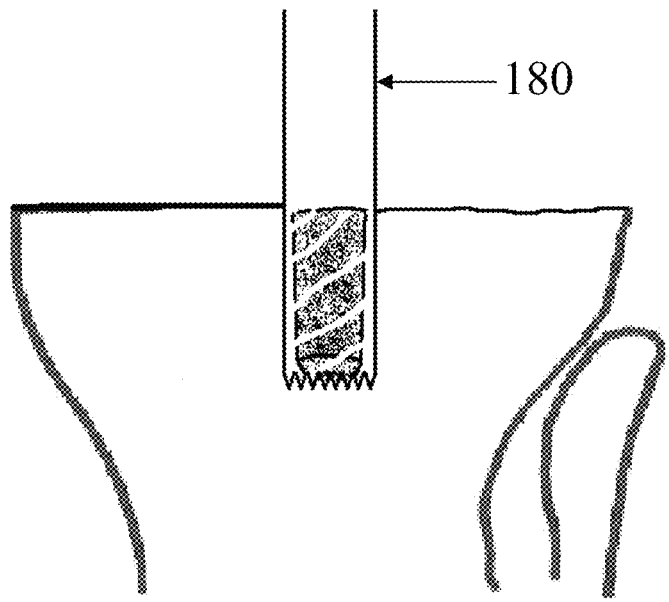
Figure 5E:
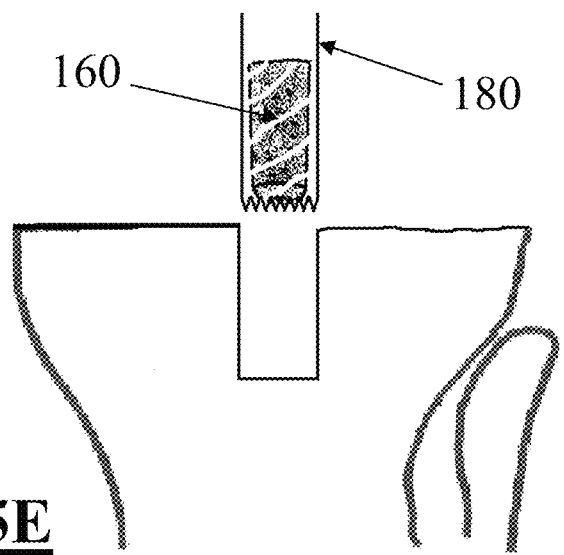

In various embodiments, pegs 160a,b can easily be separated from the tibial implant by advancing a saw or drill along the bone-facing surface of the implant (in a region between the native bone and the bone-facing side of the implant) and cutting the base of the peg at the porous region (see FIG. 5A). Once the peg has been severed, the implant can be removed from the femur (see FIG. 5B). Depending upon the surgical objectives as well as the revision implant components to be used, the pegs may be removed (e.g., using a coring drill 180 or other surgical tools well known in the art—see FIGS. 5C through 5E), or the peg can remain within the anatomy, with a subsequent revision implant covering, "capping" or otherwise reattaching to some or all of the peg, if desired.

Figure 6:
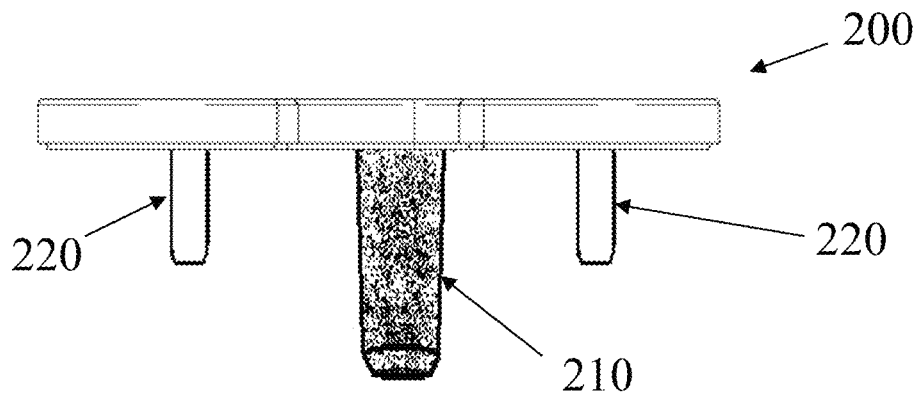
FIG. 6 depicts a side plan view of an alternative embodiment of a tibial tray implant.

In various alternative embodiments, a plurality of pegs could be used to anchor an implant to a targeted anatomical region, with one or more of the anchoring pegs including a weakened section that facilitates removal of the implant from bone, as previously described. For example, FIG. 6 depicts a tibial tray implant 200 having a plurality of anchoring pegs extending from a lower, bone-facing surface for securement to a tibial surface (not shown). The anchoring pegs can include a centrally-located porous peg 210 that provides for bony ingrowth and/or cement fixation, and peripherally placed pegs 220 which can comprise press-fit or other attachment arrangements. This arrangement will desirably provide significantly more short-term and long-term fixation for the implant as compared to an implant having only a single anchoring peg and/or single type of fixation (i.e., only one of press-fit, cement fixation and/or bone ingrowth, for example). To separate this implant from the surrounding anatomy, the surgeon may elect to tunnel under the implant (as previously described) and avoid and/or sever the peripheral pegs (at the surgeon's option), and subsequently sever or fracture the centrally-located peg 210. Desirably, the central peg 210 can be easily fractured and/or cut, as it desirably comprises a porous and/or weakened structure, as previously described. The peripheral pegs may be of a smaller size and thus more easily broken or severed, or if not severed, the peripheral pegs may be easily withdrawn from the tibia if natural tissues and/or cement have not adhered to these relatively smoother peripheral pegs. Once the implant has been removed, the central peg 210 may remain within the tibia, or it may be removed as previously described.

Figure 7:
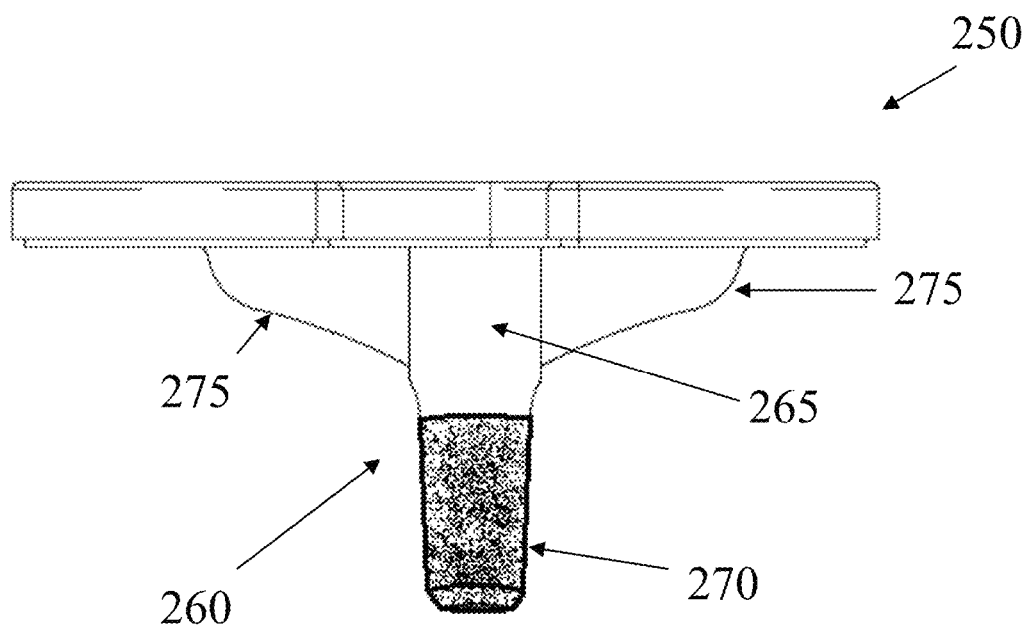
FIG. 7 depicts a side plan view of another alternative embodiment of a tibial tray implant.
Figure 8A:
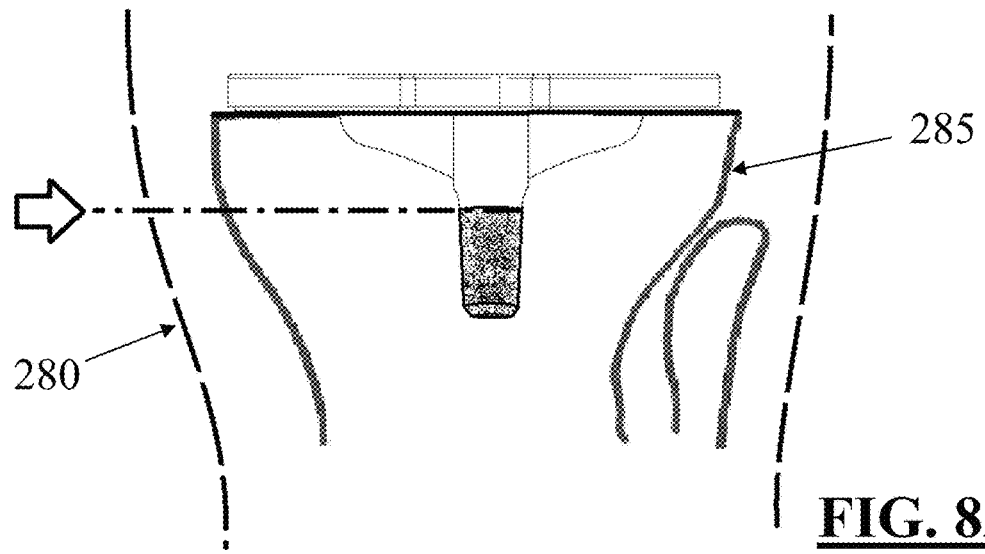
FIGS. 8A through 8C depict exemplary surgical steps for removing the implant of FIG. 7 from a patient's anatomy.
Figure 8B:
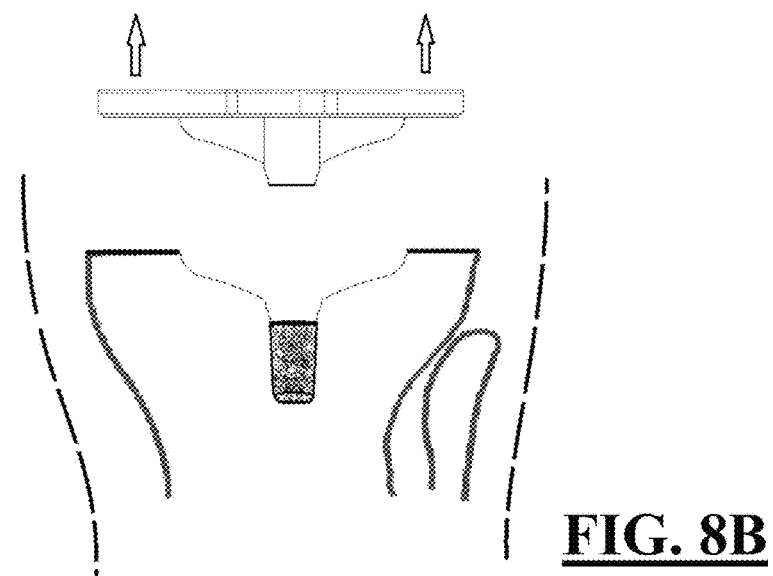
Figure 8C:
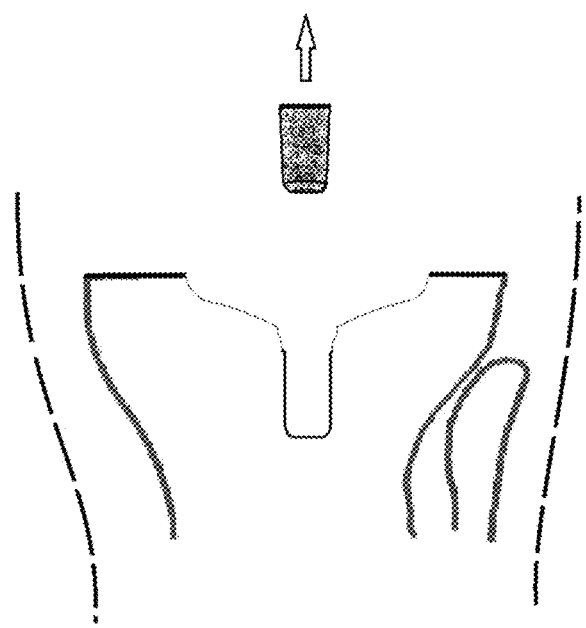

FIG. 7 depicts an alternative embodiment which includes a tibial tray 250 having a composite anchoring peg 260 that incorporates a solid proximal portion 265 and a porous distal portion 270. Also includes are one or more wings 275 that can desirably provide rotational stability to the tray 250, as known in the art. In use, the composite anchoring peg 260 can be inserted in a known manner, with the proximal portion 265 of the peg providing a press-fit securement, and the distal portion 270 desirably allowing for bony ingrowth. If revision of the tray 250 is desired, a surgical tool can be inserted into and through a patient's soft tissues 280 and tibial bone 285 from a lateral aspect, and the anchoring peg 260 can be severed at a location proximate a boundary between the proximal portion 265 and the distal portion 270 (see FIG. 8A). This desirably will release the tray 250 from the securely anchored porous distal portion 270, and allow the tray 250 to be withdrawn from the tibia (see FIG. 8B). If desired, the distal portion may remain permanently within the bone, or if may be removed using a coring drill or other tool (see FIG. 8C).

By facilitating the severing and/or fracture of anchoring elements in a less-invasive manner, the disclosed embodiments provide for removal of relevant implant components and/or anchor portions in a least-invasive manner, thereby preserving significantly more bone and/or other anatomical support structures for the subsequent revision procedure. Moreover, depending upon the chosen revision implant components and procedure, one or more residual anchoring components still secured to the bone may be used to provide additional fixation for the revision components.

In various embodiments, the implant component can include guiding features that facilitate the use of surgical tools in accessing various adaptable features. For example, a bone facing and/or peripheral edge of the implant could include markings and/or protrusions/indentations that facilitate and/or guide the advancement of a surgical cutting tool. Because the anchoring pegs can be located in various locations, and because such implants are often difficult and/or impossible to accurately visualize using x-rays or other non-invasive methods, the inclusion of such markings and/or guiding features can significantly improve the ability of the surgeon to accurately access the pegs, as well as significantly reduce unnecessary damage to the surrounding anatomy.

In various alternative embodiments, a guide tool or jig may be provided that includes guiding features and/or implant-specific surfaces that conform to various implant surfaces (and/or protrusions/indentations on the implant surface) and/or native anatomical features that desirably guide surgical tools into contact with the relevant adaptable structures. Such guiding features and implant-specific surfaces may be designed using implant data saved from a prior surgery, or such data may be constructed using patient-specific image data, if available.

Figure 9A:
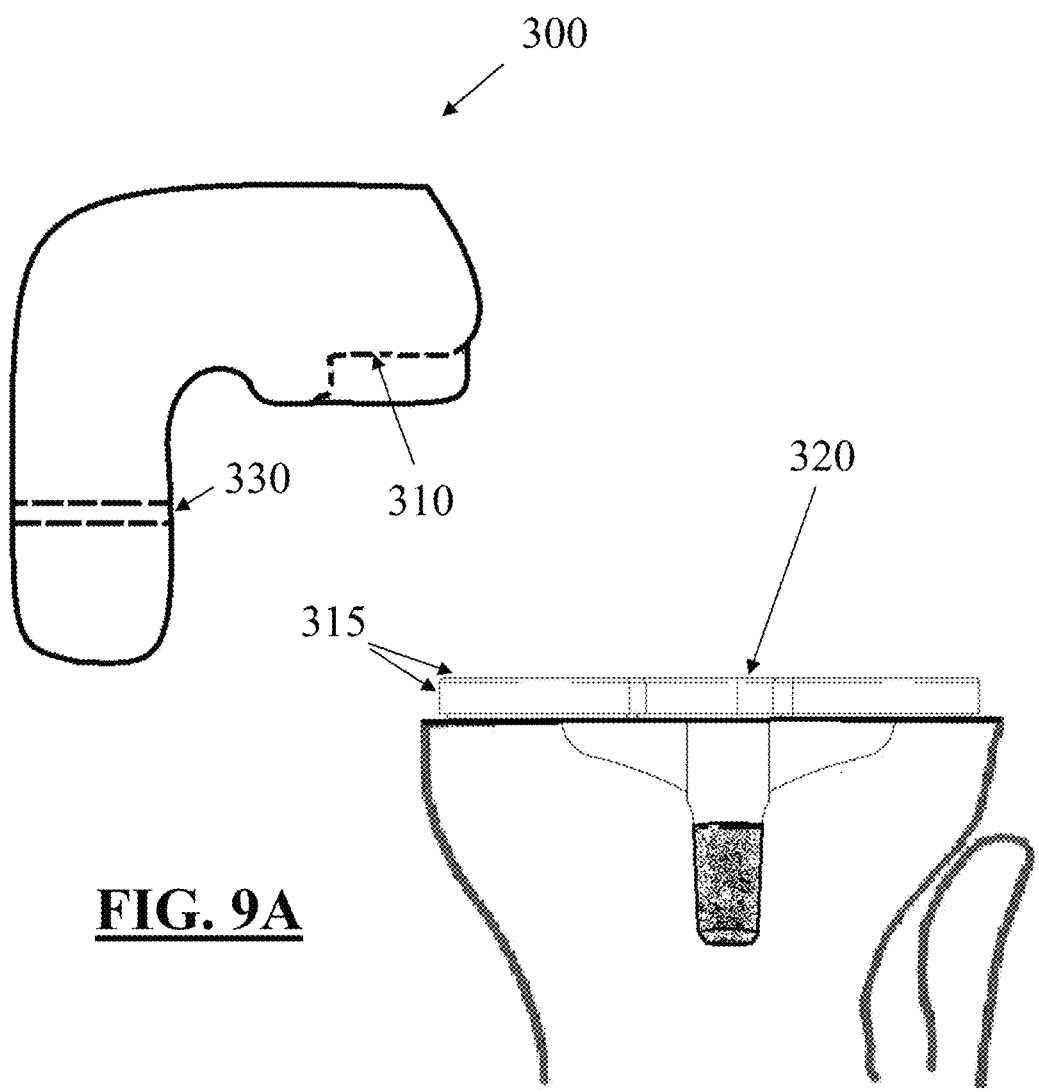
FIGS. 9A and 9B depict one embodiment of a guide tool for use in removing the implant of FIG. 7 from a patient's anatomy.
Figure 9B:
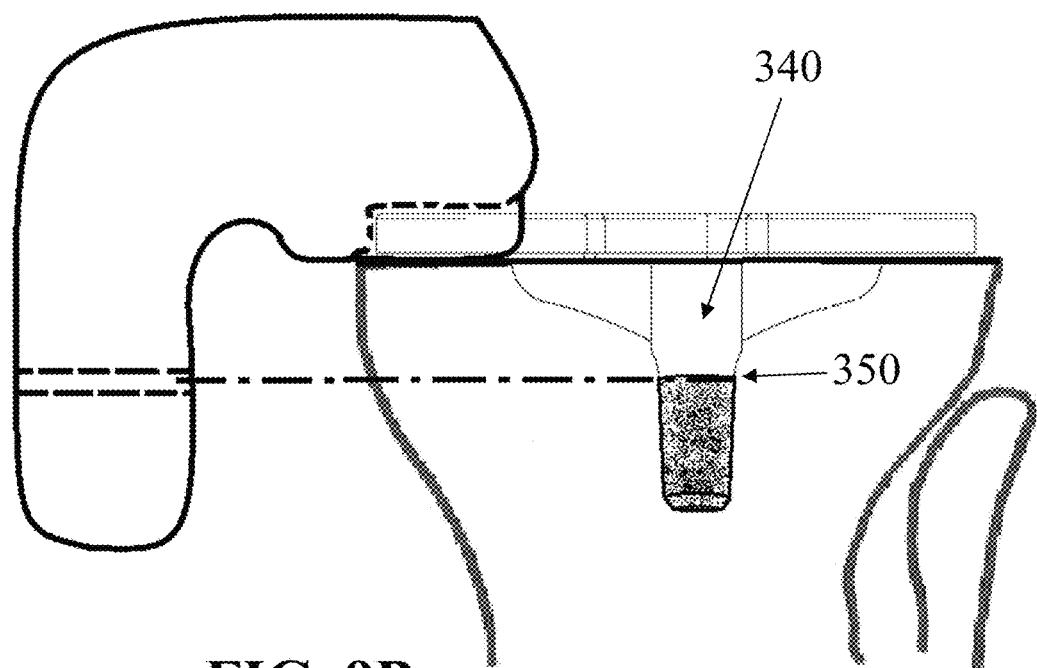

For example, a guide tool 300 as depicted in FIG. 9A can include a patient-specific surface 310 that desirably conforms to one or more exposed surfaces 315 of an implant 320. The guide tool 300 can include one or more alignment apertures 330 which provide for the controlled insertion and advancement on one or more cutting tools along a specific trajectory, which in this embodiment intersects an implant anchoring post 340 at a location proximate a solid/porous interface 350 (see FIG. 9B).

Internal Voids

In various alternative embodiments, an implant component can include features such as internal voids and/or cavities that facilitate surgical removal and/or subsequent use. For example, SLM manufacturing techniques can be utilized to create an implant component with anchoring pegs having internal voids or other features that facilitate their subsequent removal if necessary. Such features can include a central bore region formed in a cylindrical anchoring peg that, when the peg is separated from the implant (such as, for example, as previously described herein), the resected surface of the peg exposes a central bore which can be utilized to remove the peg from the surrounding bony anatomy. If desired, a drill or other surgical tool can be advanced into the bore, and attached to a slap hammer or other device which is employed in a known manner to remove the peg. In various alternative embodiments, the exposed central bore of the peg could be utilized to anchor a subsequent implant, if desired.

Improved Visualization

In various embodiments, adaptable features such as SFF manufactured voids and/or porous areas of lower material density can be employed to improve and/or facilitate non-invasive visualization (e.g., x-ray imaging or other techniques) of implant structures and/or bone interface regions (e.g., lucent lines, bone ingrowth, etc.) for a variety of reasons, including the detection of implant fatigue, fracture and/or loosening of implant components from the underlying bony anatomy. In various embodiments, the features may act as "windows" to facilitate the visualization of lucent lines or other anatomical/implant features.

FEA Analysis

Various embodiments disclosed herein will desirably include a FEA or other analysis of relevant implant datasets, which optionally may include analyses of material property information particular to the type of manufacturing processes as well as the design and/or orientation of the implant (as oriented and positioned in the intended build plan). Such an analysis can occur immediately prior to SLM manufacture (e.g., FEA analysis of each object in the build plan, with relevant manufacturing and orientation data, can be evaluated) or the analysis may be conducted on some subset thereof at any point in the evaluation and virtual packing process. The FEA analysis will desirably identify and/or highlight one or more locations of high stress and/or areas of localized implant weakness, including those that may be particular to the type of manufacturing processes as well as the design and orientation of the implant. Where FEA analysis of a part design and/or orientation identifies one or more undesired regions of potential weakness and/or failure, it may be desirous to reposition and/or reorient the object in the build plan (and/or may necessitate modifying the implant design and/or build plan in some manner). Moreover, FEA analysis may be employed to ensure that one or more adaptable features (such as those described herein) have been properly designed to accommodate implant modification (e.g., fracture and/or bending) by surgical personnel.

The maximum principal stress observed in FEA analysis can be used to establish an acceptable minimum implant thickness for an implant component having a particular size and, optionally, for a particular patient (e.g., having a particular weight, age, activity level, etc). In certain embodiments, an implant component design or selection can depend, at least in part, on a threshold minimum implant component thickness. In turn, the threshold minimum implant component thickness can depend, at least in part, on patient-specific data, such as condylar width, femoral transepicondylar axis length, and/or the patient's specific weight. In this way, the threshold implant thickness, and/or any implant component feature, can be adapted to a particular patient based on a combination of patient-specific geometric data and on patient-specific anthropometric data. This approach can apply to any implant component feature for any joint, for example, the knee, the hip, or the shoulder.

In various embodiments, the design of a given implant component and/or various features therein can be further assessed and/or modified by including FEA modeling and/or analysis, either alone or in combination with information relating to the specific manufacturing method chosen for creating the implant. For example, the creation of an implant using SLM manufacturing methods may produce an implant having differing density, porosity, durability, fatigue strength and/or other material properties than those of an implant created through traditional casting techniques. A finite element analysis (FEA) of an SLM implant and/or intended implant design may identify areas of the implant/design prone to increased and/or excessive loads, which may induce the designer to modify the design to better accommodate the anticipated loading (e.g., increase the local or global implant thickness and/or alter implant geometry or location of planar surfaces). If desired, such an FEA analysis may identify areas of concern that may impel a redesign of the implant to alleviate strength, durability and/or adaptability concerns.

In a similar manner, an FEA analysis may identify areas of one or more build objects that could benefit from some modification of the intended manufacturing process at one or more times part-way through the manufacturing process (e.g., "cross-hatching" or remelting an individual portion of a melt layer to reduce/avoid the formation of interconnected porosity and/or buckling deformation in a localized manner), and then continuing the layer deposition and laser melting process to complete the implant manufacture. If desired, the material properties (and/or potentially one or more component materials) of an implant can be varied to accommodate unique or localized requirements. For example, it may be desirable for the porosity and/or tensile strength/elasticity of a material in a femoral implant component to vary along the surface or cross-sectional profile of the implant. In a similar manner, it may be desirous for a surface of such an implant to possess differing mechanical properties than subsurface portions of the implant. Likewise, it may be desirous for a periphery of such an implant to possess differing mechanical properties than central portions of the implant. In such a case, it may be advantageous to alter the material properties of such an implant in some manner, such as by altering the laser speed, power, duration and/or remelting one or melt layers (or portions thereof such as, for example, implant surfaces portions only) to accommodate the varying demands placed upon the implant. Alternatively, the implant may comprise various materials that are adhered, layered or otherwise arranged in some fashion, including the use of multiple types of materials and/or material properties in non-aligned layers (e.g., a composite-like layering materials), to accomplish various objectives of various embodiments disclosed herein.

In a similar manner, implants comprising metals, plastics and/or ceramic constituents may be formed of two or more materials, or may comprise a single material with sections or portions having varying material characteristics (e.g., by radiation, heating, cooling, hipping, annealing, chemical action, work hardening, peening, carburizing, hardening, surface treating, oxidation, etc.) For example, the medial and/or lateral and/or superior and/or inferior portions of a tibial tray inset may be formed from two or more materials adhered or otherwise connected in some manner, each material having a unique material property, resulting in an implant with differing mechanical properties on its medial and/or lateral and/or superior and/or inferior sides. Such an implant could alternatively comprise a multi-layered material, with different materials and/or material properties exposed on the surface during a subsequent machining process (with the processing tools extending to differing depths), thereby resulting in a generally uniform layered material with different surface properties on the surface of its medial and lateral sides.

Materials

Any material known in the art can be used for any of the implant systems and component described in the foregoing embodiments, for example including, but not limited to metal, metallic powders, metal alloys, combinations of metals, ceramics, plastic, polyethylene, cross-linked polyethylene's or polymers or plastics, pyrolytic carbon, nanotubes and carbons, as well as biologic materials.

In various exemplary embodiments, the DMLS/SLM raw material can comprise a CrCo powder having an average particle size of between 34 and 54 microns, although larger and/or smaller particles may be used with varying degrees of utility (as well as the use of differing size particles in creating a single implant component). In various embodiments, the deposed particle layer may be approximately 60 microns thick which, when melted, consolidated and cooled, can create a solid structural layer of approximately 20 microns thickness.

Any fixation techniques and combinations thereof known in the art can be used for any of the implant systems and component described in the foregoing embodiments, for example including, but not limited to cementing techniques, porous coating of at least portions of an implant component, press fit techniques of at least a portion of an implant, ingrowth techniques, etc.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

What is claimed is:

1. A tibial implant component, the tibial implant component comprising: a tibial tray; at least one anchoring peg extending from a bone-facing surface of the tibial tray; wherein the tibial tray is a substantially solid structure, wherein at least a proximal portion of the anchoring peg consists of a lattice structure comprising a plurality of generally straight individual filaments, the lattice structure extending across a cross-section of the anchoring peg; and wherein the tibial tray and the anchoring peg are configured such that the tibial tray can be intraoperatively separated from the anchoring peg, when the anchoring peg is positioned within a patient's tibia, by directing a cutting tool along the bone-facing surface of the tibial tray and cutting through at least a portion of the lattice structure.

2. The tibial implant component of claim 1, wherein at least one dimension of the tibial tray is based on patient-specific information.

3. The tibial implant component of claim 2, wherein the patient-specific information includes electronic image data of a knee joint of the individual patient.

4. The tibial implant component of claim 2, wherein the patient-specific information includes size and/or shape information regarding a knee joint of the individual patient.

5. The tibial implant component of claim 1, wherein at least one dimension of the anchoring peg is based on patient-specific information.

6. The tibial implant component of claim 5, wherein the patient-specific information includes electronic image data of a knee joint of the individual patient.

7. The tibial implant component of claim 5, wherein the patient-specific information includes size and/or shape information regarding a knee joint of the individual patient.

8. An implant component comprising: a first implant portion including a substantially solid structure, the first implant portion having a bone-facing surface; an anchoring peg extending from the bone-facing surface, the anchoring peg comprising a porous portion, the porous portion extending across a cross-section of the anchoring peg; wherein the first implant portion and the anchoring peg are integral and formed of a single material; and wherein the first implant portion and the anchoring peg are configured such that the first implant portion can be intraoperatively separated from at least a portion of the anchoring peg, when the anchoring peg is positioned in a patient's tissue, by directing a cutting tool through at least a portion of the porous portion.

9. The implant component of claim 8, wherein the anchoring peg comprises a solid portion positioned between the porous portion and the first implant portion.

10. The implant component of claim 8, wherein at least one dimension of the anchoring peg is based on patient-specific information.

* * * * *